US 8,019,407 B2

(12) United States Patent
Lian et al.

(10) Patent No.: US 8,019,407 B2
(45) Date of Patent: Sep. 13, 2011

(54) HEART MONITORING DEVICE AND METHOD

(75) Inventors: Jie Lian, Beaverton, OR (US); Dirk Muessig, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 341 days.

(21) Appl. No.: 12/257,578

(22) Filed: Oct. 24, 2008

(65) Prior Publication Data

US 2010/0106033 A1    Apr. 29, 2010

(51) Int. Cl.
*A61B 5/04* (2006.01)

(52) U.S. Cl. ......................... 600/509; 600/516; 600/523

(58) Field of Classification Search ........... 600/508–528
See application file for complete search history.

(56) References Cited

U.S. PATENT DOCUMENTS

| | | | |
|---|---|---|---|
| 5,285,793 A | 2/1994 | Slovut et al. | |
| 5,682,901 A * | 11/1997 | Kamen | 600/519 |
| 5,891,048 A | 4/1999 | Nigam | |
| 6,470,215 B1 | 10/2002 | Kraus | |
| 6,574,509 B1 | 6/2003 | Kraus | |
| 6,622,043 B1 | 9/2003 | Kraus | |
| 6,656,126 B2 * | 12/2003 | Starobin et al. | 600/508 |
| 6,922,584 B2 | 7/2005 | Wang et al. | |
| 6,937,887 B2 | 8/2005 | Bock | |
| 7,031,765 B2 | 4/2006 | Ritscher et al. | |
| 7,072,709 B2 * | 7/2006 | Xue | 600/509 |
| 7,353,057 B2 | 4/2008 | Schiessle et al. | |
| 7,502,643 B2 * | 3/2009 | Farringdon et al. | 600/509 |
| 2005/0004486 A1 * | 1/2005 | Glass et al. | 600/515 |
| 2005/0171447 A1 | 8/2005 | Esperer | |
| 2006/0084883 A1 | 4/2006 | Linker | |
| 2006/0247548 A1 | 11/2006 | Sarkar et al. | |
| 2007/0066906 A1 | 3/2007 | Goldberger et al. | |
| 2007/0265667 A1 | 11/2007 | Muessig | |

FOREIGN PATENT DOCUMENTS

WO    WO2006/118854    11/2006

OTHER PUBLICATIONS

Esperer, Hans D. et al., "Cardiac arrhythmias imprint specific signatures on Lorenz plots", Annals of Noninvasive Electrocardiology, vol. 13, No. 1, Jan. 2008, pp. 44-60.
Hnatkova, K. et al. "Numeric processing of Lorenz plots of R-R intervals from long-term ECGs", Journal of Electrocardiology, vol. 28, No. Suppl., Jan. 1, 1995, pp. 74-80.
European Search Report for Application No. EP 09 17 0268, dated Feb. 5, 2010, 8 pages.

* cited by examiner

*Primary Examiner* — Niketa Patel
*Assistant Examiner* — Catherine Voorhees
(74) *Attorney, Agent, or Firm* — ARC IP Law, PC; Joseph J. Mayo

(57) ABSTRACT

A heart monitor for processing input signals that represent periodically reoccurring events in a sequence of heart cycles. According to the invention graphical data representing a scatter plot of at least two dimensions, one dimension representing interval duration or its inverse and the other dimension representing change of duration or its inverse, respectively, are generated. The scatter plot comprises data points of which each data point represents heart interval duration or its inverse plotted against the change of duration with respect to a neighboring interval or the inverse of said change respectively.

20 Claims, 21 Drawing Sheets

HEART MONITORING DEVICE AND METHOD

BACKGROUND OF THE INVENTION

1. Field of the Invention

The present invention generally relates to medical devices that measure cardiac inter-beat intervals, analyze the said cardiac inter-beat intervals, and classify the underlying cardiac rhythm based on the said cardiac inter-beat intervals. More particularly, the present invention relates to a method and apparatus for accurate detection of atrial fibrillation based on analysis of the cardiac inter-beat intervals.

2. Description of the Related Art

The variation of cardiac inter-beat (e.g., PP, RR) intervals results from both rhythmic activity of the heart electrical source and the dynamic properties of the cardiac conduction pathway, both of which are under autonomic control. In normal sinus rhythm, the RR intervals are known to fluctuate at various time scales, a phenomenon known as heart rate variability (HRV), which has been extensively investigated to probe the autonomic nervous activity. On the other hand, structural or functional abnormalities of the cardiac electrical conduction system can lead to cardiac arrhythmias.

The RR interval is a preferred choice to represent cardiac inter-beat interval due to easy acquisition of the electrocardiogram (ECG) signals, and the prominent QRS complexes present in these signals. The RR intervals not only can be easily measured from the surface ECG, but also can be measured from the subcutaneous ECG that is recorded by placing electrodes under the skin, or from the intracardiac electrogram (IEGM) that is recorded by inserting electrodes into the heart. Alternatively, the cardiac inter-beat intervals can also be obtained from other types of biosignals that are known to show the same rhythmic variation as the cardiac beats, including but not limited to, the blood pressure signal, the transthoracic impedance signal, the pulse oximeter signal, finger plethysmography signal, etc.

Cardiac rhythm classification based on time series analysis of RR intervals has been a research thrust during the past decades, with particular focus on automatic detection of atrial fibrillation (AF). AF remains the most common clinical tachyarrhythmia that causes significant morbidity and mortality. The clinical hallmark of AF is an irregularly irregular ventricular rhythm, which is sometimes characterized as random RR intervals. Converging evidence suggests that the irregular ventricular rhythm in AF had adverse hemodynamic effects independent of the fast ventricular rate. Moreover, it is well known that AF patients have significantly higher risk of thromboembolic stroke. Presence of AF is also a strong risk factor for developing other serious, chronic heart diseases, such as dilated cardiomyopathy and congestive heart failure (HF). In addition, clinical management of AF patients requires accurate assessment of the antiarrhythmic efficacy of various therapies, e.g., drug-based rhythm control, internal or external cardioversion, catheter ablation, etc. Therefore, early detection of AF and continuous monitoring of AF burden is critically important in cardiac rhythm management.

Numerous techniques have been developed to automatically classify cardiac rhythms, in particular AF, by means of RR interval analysis. Nonetheless, all existing methods have various limitations. One typical approach for AF detection is to collect multiple beats of RR intervals and quantify their global or beat-to-beat variability by means of statistical metrics, such as mean, median, absolute deviation, etc. Representative prior arts include U.S. Pat. No. 6,922,584 issued to Wang et al., U.S. Pat. No. 6,937,887 issued to Bock, and U.S. Pat. Appl. No. 2006/0084883 by Linker. However, the specificity for AF detection using these simple variability metrics is not sufficiently high, because many other types of cardiac rhythms (e.g., exercise, frequent extra-systoles, etc.) also show large variability of RR intervals.

Some non-linear complexity measures that have been widely used in HRV analysis, e.g., sample entropy, asymmetry index, symbolic coding, etc., have also been suggested for cardiac rhythm classification, as disclosed in U.S. Pub. No. 2007/0066906 by Goldberger et al. However, these measures only reflect the global complexity of the RR intervals, whereas it is known that many types of cardiac rhythms have overlapping range of RR interval complexity, for example, AF vs. ventricular fibrillation (VF), sinus rhythm with depressed HRV (e.g., in HF patients) vs. stable sinus tachycardia, and so on.

Another non-linear approach for cardiac rhythm classification is based on the Lorenz plots, which have also been widely used in HRV analysis for the past two decades. By plotting the scatter plot of each RR interval vs. the immediately preceding RR interval, a 2D Lorenz plot is obtained which shows characteristic clusters for different types of cardiac rhythms. Similarly, 3D or higher dimensional Lorenz plot could be obtained by embedding more dimensions with more beat delays. Representative prior arts include U.S. Pat. No. 7,353,057 issued to Schiessle et al., and U.S. Pat. Pub. No. 2005/0171447. Obviously, these conventional Lorenz plots focus only on RR intervals (or heart rate) whereas the information on directional change of RR intervals (or change of heart rate) is hidden. On the other hand, cardiac rhythm classification based on Lorenz plots of dRR intervals (i.e., the difference between two adjacent RR intervals) has also been disclosed in U.S. Pat. No. 7,031,765 issued to Ritscher et al., and U.S. Pat. Pub. No. 2006/0247548 by Sarkar et al. However, by focusing on the beat-to-beat change of the RR intervals (or change of heart rate), these dRR Lorenz plots ignore the information pertaining to the raw RR intervals (or heart rate).

BRIEF SUMMARY OF THE INVENTION

It is an objective of the invention to provide a device or a method or both that provides for more robust cardiac rhythm classification.

According to the invention, this objective is achieved by a heart monitor for processing input signals representing periodically reoccurring events in a sequence of heart cycles, comprising a signal input for the signal, an event detector connected to the signal input and adapted to respond to signal features representing a reoccurring cardiac event, at least one timer connected to the event detector and adapted to determine a duration or its inverse of a time interval between each two successive signal features representing a cardiac event an interval evaluation stage connected to the timer and being adapted to determine the change of the duration of two successive intervals or the inverse thereof and a processing stage connected to the evaluation stage and the timer and being adapted to generate graphical data representing a scatter plot of at least two dimensions, one dimension representing interval duration or its inverse and the other dimension representing change of duration or its inverse, respectively, wherein the plot comprises data points of which each data point represents an interval duration or its inverse plotted against the change of duration with respect to a neighbouring interval or the inverse of said change respectively.

Preferably, the input signal is an electrocardiogram signal or a marker signal derived thereof. The markers of the marker signal correspond to cardiac events such as ventricular depolarization as represented by a QRS-complex in an electrocardiogram. The interval between each two successive signal features then would be an RR-interval and its duration corresponds to heart cycle length and its inverse is the heart rate (R). The inverse of the change of RR (dRR) interval duration corresponds to the first derivative of the heart rate (dR).

The objective is also achieved by a method of processing input signals representing periodically reoccurring events in a sequence of heart cycles, comprising the steps of obtaining a signal representing periodically reoccurring events in sequence of heart cycles, detecting signal features representing a reoccurring cardiac event, determining a duration or its inverse of a time interval between each two successive signal features representing a cardiac event, determining the change of the duration of two successive intervals or the inverse thereof and generating graphical data representing a scatter plot of at least two dimensions, one dimension representing interval duration or its inverse and the other dimension representing change of duration or its inverse, respectively, wherein the plot comprises data points of which each data point represents an interval duration or its inverse plotted against the change of duration with respect to a neighbouring interval or the inverse of said change respectively, and repeating said steps for a plurality of heart cycles.

According to this invention, an RdR plot is created by plotting RR intervals against the change of RR intervals. The scatter plot of RR vs. dRR embeds both heart rate and directional change of the heart rate information, thus offering a more complete picture of the underlying cardiac rhythm. In addition, the trajectory of the RdR plot offers both heart rate trend (i.e. increase and/or decrease) and heart rate acceleration and/or deceleration information.

Also according to the present invention, various types of cardiac rhythms could be easily identified by their characteristic clustering patterns on the RdR plots. Various metrics are introduced to separate these patterns, thus cardiac rhythm classification can be made.

According to a preferred embodiment of the heart monitor, the processing stage is connected to an analyzer stage that is adapted to process said graphical data and to detect cluster of data points in said scatter plot and to generate an output signal that depends on the location of one or more clusters of data points in said scatter plot. The analyzer stage can be adapted to compare the location of one or more clusters of data points in said scatter plot to reference data and to generate a rhythm classification output signal that depends on the similarity of the location of one or more clusters of data points in said scatter plot to said reference data.

The analyzer stage can be further adapted to generate one or more metrics that depend on the location of one or more clusters of data points and generate an output signal that depends on the relation of said metrics to predefined thresholds.

Reference data may comprise characteristic clustering patterns on the RdR plots and/or metrics related to RdR plot patterns. The reference data metrics may be also expressed as thresholds. The relation of reference data to the various types of cardiac rhythms can be obtained by methods known in the art, e.g. by a data base that contains reference data and that is verified by checkups or clinical studies.

The signal input and the event detector can be part of an implantable medical device such as an implantable pacemaker, an implantable cardioverter/defibrillator, or a subcutaneous ECG monitor.

The processing stage and the analyzer can be part of the implantable medical device, or alternatively, can be part of an external device that is adapted to be wirelessly connected to an implantable medical device that generates said input signal.

The details of the invention can be understood from the following drawings and the corresponding text descriptions.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention provides a method for automatic classification of cardiac rhythms by means of cardiac inter-beat interval analysis. The cardiac inter-beat intervals are preferably the RR intervals that are measured from the surface ECG signals (e.g., by Holter monitoring), or from the subcutaneous ECG signals (e.g., by implantable subcutaneous ECG monitoring), or from the intracardiac electrogram (e.g., by implantable pacemakers or defibrillators). Alternatively, the cardiac inter-beat intervals can also be obtained from other types of biosignals that are known to show the same rhythmic variation as the cardiac beats, including but not limited to, the blood pressure signal, the transthoracic impedance signal, the pulse oximeter signal, finger plethysmography signal, etc.

Figure 1:
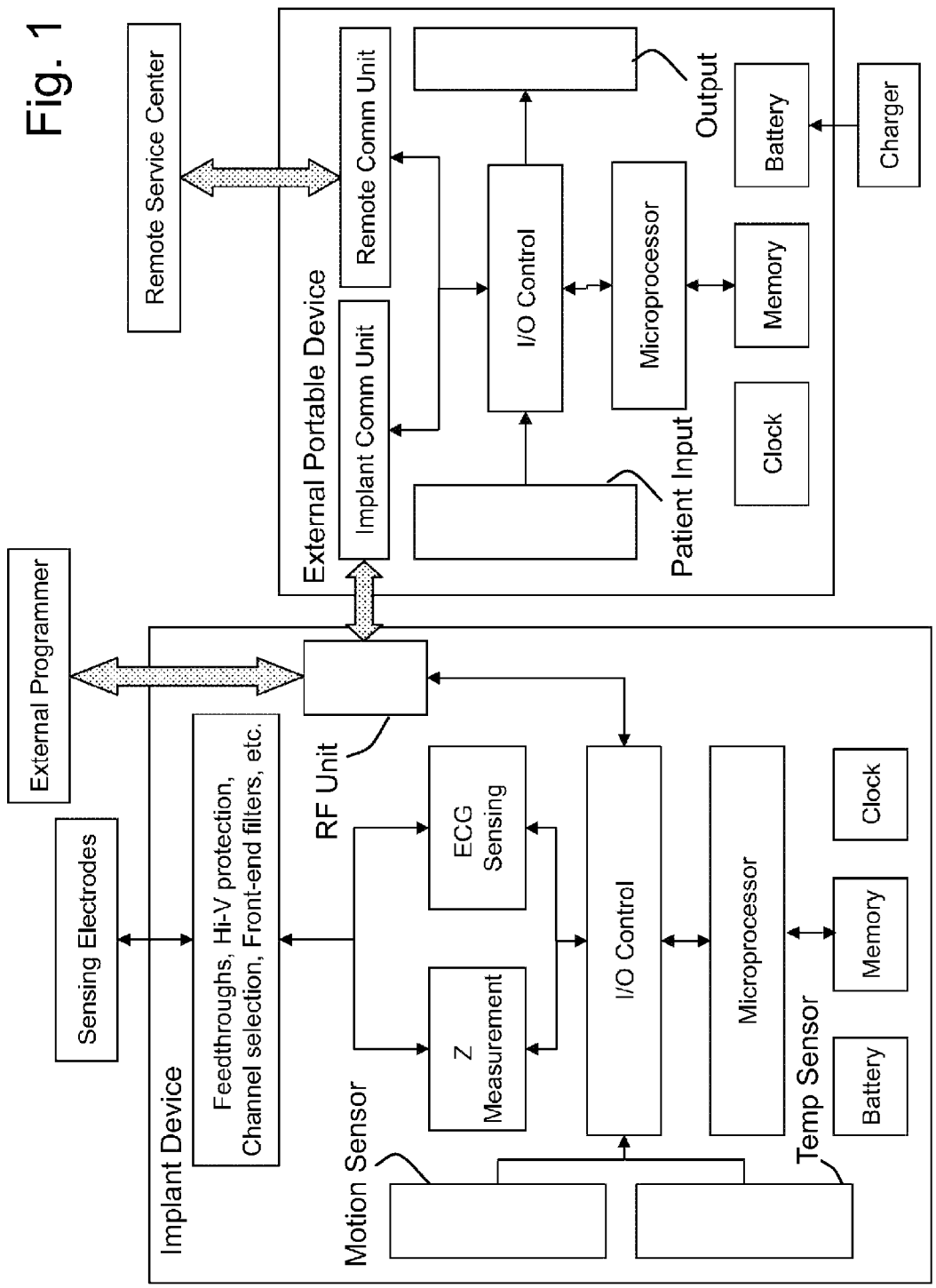
FIG. 1 shows a block diagram of an implantable device for subcutaneous ECG monitoring, and its interfaces with an external programming device and an external portable device, which further communicates with the remote service center.

FIG. 1 shows a block diagram of an implantable device for subcutaneous ECG monitoring, and its interfaces with an external programmer and an external portable device, which further communicates with the remote service center. A similar apparatus, yet with different application for semi-automatic atrial defibrillation, has been described in U.S. Pat. Appl. No. US2007/0265667 filed by the present assignee.

Refer to FIG. 1. The implantable device consists of an electronic circuitry that is hermetically sealed inside a Can, which is made from a biocompatible conductive material such as titanium, a non-conductive header attached to the Can, two or more sensing electrodes, with or without leads connected to the header.

The sensing electrodes, which are electrically isolated from one another, are mounted over the outer surface of the Can, or outside the header, or at the distal end of the leads (if available). For subcutaneous ECG recording, one ore more pairs of sensing electrodes form the sensing vectors and the inter-electrode distance is preferably greater than 3 cm.

The leads are optional for subcutaneous ECG recording. Generally, if the measured subcutaneous ECG amplitude is too small for reliable sensing, despite configuring different sensing vectors and recording at different anatomical locations, then one or more subcutaneous leads (with distal electrodes) could be tunneled under the patient's skin and connected to the header, so that larger subcutaneous ECG amplitude could be measured by increasing inter-electrode distance, e.g., between the lead electrode and the Can or header electrode.

Still referring to FIG. 1, enclosed inside the hermetically sealed Can, a microprocessor and associated circuitry make up the controller of the implant device. The implant device is powered by a battery, and maintains an internal clock for timing the operations. The microprocessor communicates with a memory via a bi-directional data bus. The memory typically comprises a ROM or RAM for program storage and a RAM for data storage.

The sensing electrodes are first connected to an electronic interface that preferably includes a feedthrough circuitry for noise reduction, a high voltage protection circuitry, a switch network circuitry for sensing channel selection, and front-end analog filters, as well known in the field. The configurations of the interface circuitry (e.g., filter settings, sensing channel selection, etc.) can be programmed by the microprocessor.

The microprocessor connects to an I/O control unit to manage the input and output of the implant device. One input signal is the subcutaneous ECG picked up by the sensing electrodes. After pre-processed by the interface circuitry, the subcutaneous ECG signal is further processed by the ECG sensing unit, which usually consists of amplifiers, analog-to-digital converters, digital filters, etc., as known in the art.

Another input signal is the impedance (Z) signal measured between the sensing electrodes. By injecting a small constant current (e.g., 100 uA, preferably biphasic) between two electrodes while measuring the voltage difference between the same or different pair of electrodes, the impedance is calculated as the ratio between the measured voltage difference and the injecting current strength. As known in the art, the impedance signal provides useful information on the integrity of the sensing channel. In addition, the continuously measured impedance signal may be further processed by the microprocessor to extract other physiological status of the patient, such as the respiration rate.

Other types of biological signals measured by specific sensors can also serve as input to the implant device. For example, an on-board accelerometer can serve as a motion sensor that provides patient's activity signal to the implant device, an on-board (or embedded in the lead) temperature sensor can provides the subcutaneous temperature signal to the implant device. Other types of input signals include, but are not limited to, the subcutaneous pressure signal measured by a pressure sensor, the acoustic signal measured by an acoustic sensor, the subcutaneous pH signal measured by a pH sensor, etc.

By running the program stored in the memory, the microprocessor also sends instructions to the ECG sensing unit, the impedance measurement unit, and other input measurement units to control how these signals are acquired (e.g., gain, offset, filter settings, sampling frequency, sampling resolution, etc.).

The acquired biological signals are then stored in the device memory and analyzed by the microprocessor by running programmed algorithms. For example, the microprocessor continuously analyzes the acquired subcutaneous ECG signals to detect the peak of QRS complex. Such QRS peak detection can be achieved by many different means. In a preferred embodiment, the QRS peak detection is achieved by using an Auto-Sensing algorithm that automatically adjust the sensing threshold, which is adaptive to the measured peak amplitude of the QRS complex and varies based on a predetermined time dependence. One exemplary Auto-Sensing algorithm has been disclosed in U.S. Pat. No. 5,891,048, assigned to the present assignee.

Accordingly, the implant device measures the intervals between any two adjacent peaks of the detected QRS complexes, and these intervals are termed RR intervals. These measured RR intervals are stored in the device memory according to predefined storage modes. One typical mode is the queue-loop mode, meaning the measured RR intervals are stored in a predefined memory space, and while the allocated memory space is full, the newly measured RR intervals replace the oldest stored RR interval data. Another typical mode is the snapshot mode, meaning the measured RR intervals are stored in a predefined memory space, and while the allocated memory space is full, the newly measured RR intervals are not stored until the microprocessor decides to store another episode of RR intervals. Yet another typical mode is the mixed mode, in which one or more segments of allocated memory space store the RR intervals in queue-loop mode, whereas one or more segments of separately allocated memory space store the RR intervals in snapshot mode.

Similarly, the microprocessor can also continuously analyze the acquired subcutaneous ECG signals to measure other metrics of the QRS complex, such as the width of the QRS complex, the positive or negative peak amplitude of the QRS complex, the absolute area under the QRS complex, the maximum positive or negative slopes of the QRS complex, the dominant frequency component of the QRS complex, the complexity measures (e.g., sampled entropy) of the QRS complex, and so on. Likewise, the time series of these measured metrics are stored in the device memory for further analysis.

The implant device also includes a radio-frequency (RF) telemetry unit. The RF telemetry unit may be of the type well known in the art for conveying various information which it obtains from the implant device to the external programmer, or for receiving programming parameters from the external programmer and then conveys to the implant device. In one typical embodiment, the external programmer can interrogate the implant device to get the status of the implant device (e.g., battery status, sensing channel impedance, etc.) or the data recorded by the implant device (e.g., peak amplitude of the QRS complexes, statistics of measured RR intervals, etc.). In another typical embodiment, the external programmer can be used to activate or deactivate selected algorithms or update programmable parameters of the implant device.

In addition, the external portable device to be described hereinafter, can also communicate bi-directionally with the implant device through the telemetry unit. Preferably, the data that may be received from or sent to the external portable device are more limited as compared to the data that may be received from or sent to the external programmer.

In a preferred embodiment, the data that are transmitted from the external portable device to the implant device are simple commands, such as trigger a snapshot of the acquired subcutaneous ECG, retrieve most recently diagnostic information from the implant device, etc. These commands set the implant device into one of a number of modalities wherein each modality is determined and controlled by parameters that can only be selected by a physician operating the external programmer using secure password or codes.

The data that are transmitted from the implant device to the external portable device preferably include simple acknowledgment to confirm receiving the commands from the external portable device, the signals warning the detection of abnormal conditions, such as detection of atrial fibrillation (AF), detection of high ventricular rate (HVR), detection of low ventricular rate (LVR), detection of abnormal sensing impedance, detection of abnormal temperature, and so on. Other diagnostic information, such as the AF burden, the frequency of ectopic beats, snapshots of RR intervals or subcutaneous ECG, etc., can also be transmitted to the external portable device. Preferably, a physician operating the external programmer using secure password or codes controls the enable or disable condition as well as the amount of data that can be transmitted from the implant device to the external portable device.

Still referring to FIG. 1, the external portable device has a power source, such as a lithium battery, which provides power to the electrical components of the device. The battery is chargeable by connecting to an external charger. The external portable device also maintains an internal clock for timing its operations. The overall functioning of the external portable device is controlled by its microprocessor, which reads and performs instructions stored in its associated memory. The instructions stored in memory preferably include instructions defining a communication protocol compatible with the implant device, and instructions defining a communication protocol compatible with the remote service center.

The microprocessor of the external portal device communicates with an I/O control unit to read from the keypad (or press switches) the patient input commands. In an exemplary embodiment, one subset of the input commands is designed to configure the external portable device, for example, to turn on or off certain outputs as described hereinafter, or select specific communication protocols. Another subset of the input commands is designed to establish communication between the external portable device and the remote service center through remote communication unit. For example, patient's input can command the external portable device to transmit diagnostic information (retrieved from the implant device) to the remote service center, and wait to receive acknowledgement. The third subset of the commands is designed to establish communication between the external portable device and the implant device through implant communication unit. For example, patient's input can command the external portable device to transmit corresponding signals to the implant device to trigger recording a snapshot of the subcutaneous ECG, to retrieve diagnostic information from the implanted device, etc. The implant communication unit also receives the acknowledgement and related diagnostic information sent from the implant device, and conveys these data to the microprocessor for storage in the memory.

According to one exemplary embodiment of the present invention, upon receiving a predefined warning signal from the implant device (e.g., detection of AF, detection of HVR, detection of LVR, detection of abnormal sensing impedance, detection of abnormal temperature, etc.), the microprocessor of the external portable device communicates with the I/O control unit to generate output that is perceptible by the patient. Such output can be in the form of visible message, such as the light-up or blinking of a light emitting diode (LED) or the text message displayed in a liquid crystal display (LCD), or in the form of audible message such as beep, ringing tone, or pre-recorded voice messages played by a speaker, or in the form of discernible vibration by a vibrator. According to the patient's preference, one or multiple types of warning message can be respectively turned on or off. For example, the visible warning message can be turned on while the audible warning message can be turned off during the night if the patient chooses not to be disturbed during sleep even if the implant device detects AF. Besides generating warning messages, some diagnostic information that is received from the implant device and stored in memory (e.g., the heart rate) can also be provided to the patient in the form of visual or audible messages.

The external portable device, via its remote communication unit, can further communicate with the remote service center. Such long-range communication apparatus can be in the form of a mobile radio network, or a fixed-line telecommunication network, or the internet, as well known in the art. Examples of such long-range communication apparatus have been taught in U.S. Pat. Nos. 6,470,215, 6,574,509, 6,622, 043, all are assigned to the assignee of the present invention and are hereby incorporated herein by reference.

In one typical embodiment, the external portable device transmits the implant device status information (e.g., battery status, sensing impedance, etc.) as well as relevant diagnostic information (e.g., AF burden, EB frequency, etc.) to the remote service center according to a predefined transmission frequency and schedule (e.g., every midnight, etc.). Yet in another typical embodiment, the external portable device communicates with the remote service center in a trigger mode, for example, upon receiving a warning signal from the implant device, or upon the patient trigger. In such cases, the external portable device transmits critical diagnostic information stored in memory (e.g., AF burden, mean heart rate, the subcutaneous ECG snapshot, etc.) to the remote service center.

The remote service center receives the information via compatible communication protocols, then sends acknowledgement back to the external portable device, which may generate visible or audible output indicating receipt of the acknowledgement. The data received by the remote service center is stored in central database, and is promptly presented to the patient's physician or responsible expert through proper means, such as fax or email as known in the art. By reviewing the received diagnostic information, the physician can evaluate the patient's condition and provide expert advice to the patient who wishes to contact the physician before taking any action in response to the warning signals generated by the external portable device.

According to this invention, the device continuously senses the subcutaneous ECG signals, detects the peak of QRS complex, and measures the RR intervals. The device also maintains a first-in-first-out (FIFO) running buffer that stores the measured RR intervals of the most recent L+1 cardiac cycles, where L is a predefined parameter that can be programmed through the external programming device.

Also according to this invention, the rhythm classification is triggered when and only when the measured heart rate exceeds a programmed physiological zone, defined by a high rate limit (HRL) and a low rate limit (LRL). In one embodiment, HRL is 100 bpm (corresponding to RR interval 600 ms), and LRL is 40 bpm (corresponding to RR interval 1500 ms). Preferably, the heart rate is continuously measured by calculating the mean or median value of the most recent K RR intervals, where K≦L+1 is a predefined parameter that can be programmed through the external programming device.

Generally speaking, smaller K is preferred for faster arrhythmia detection, whereas larger L is preferred for more robust rhythm classification. In a typical embodiment, K can be selected from the set {4, 8, 16, 32}, and L can be selected from the set {16, 32, 64, 128}.

Figure 2:
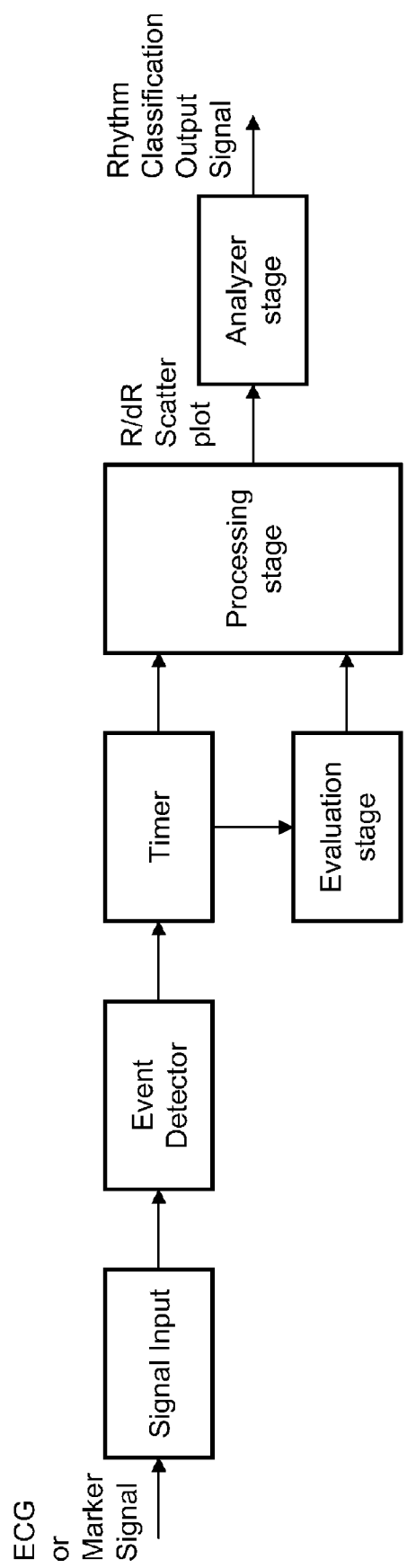
FIG. 2 shows a block diagram of a heart monitor according to the invention.

FIG. 2 is a more detailed representation of a heart monitor according to a preferred embodiment of the invention. The heart monitor as implemented by the implant device or the external portable device or both of FIG. 1 comprises a signal input that can receive an electrocardiogram signal. Connected to the signal input is an event detector that is adapted to detect cardiac events in said input signal. If the input signal is an intracardiac electrogram, the cardiac events to be detected can be ventricular depolarizations that manifest in signal features called QRS complex in an electrocardiogram. Such QRS complexes can be detected by way of comparing the input signal to a predetermined threshold or by the Auto-Sensing algorithm disclosed in U.S. Pat. No. 5,891,048, assigned to the present assignee.

A timer connected to the event detector is adapted to determine the duration of each time interval between each two successive cardiac events. This time interval corresponds to the heart cycle length and can be an RR-interval. The inverse of the heart cycle length would be the heart rate. An evaluation stage connected to the timer is adapted to determine a change of duration of the RR-interval for each heart cycle. A processing stage connected to both, the timer and the evaluation stage, is adapted to generate a scatter plot comprising data points. Each data point represents a heart cycle length (duration of RR-interval) plotted against the change of heart cycle length compared to previous heart cycle. Alternatively, the processing stage is adapted to plot the inverse of heart cycle length, that is the heart rate, against the change of heart rate. The processing stage is adapted to generate a plurality of data points representing a plurality of heart cycles. An analyzer stage connected to the processing stage is adapted to determine cluster of data points in the scatter plot generated by the processing stage and to compare the location of these clusters to reference data stored in a memory of the device. By way of this comparison, a rhythm classification output signal is generated by the analyzer stage. The rhythm classification output signal indicates whether or not the analyzed heart rhythm is stable or not, or exhibits a behavior characteristic for a certain heart rhythm.

Now the method to classify the cardiac rhythm based on device stored most recent RR intervals is disclosed. Denote {RR(i)} the series of RR intervals collected by the monitoring device, where RR(i) represents the i-th RR interval and $0 \leq i \leq L$. Further denote {dRR(i)} the series of differences between adjacent two RR intervals. According to one typical embodiment of the present invention, dRR(i)=RR(i)−RR(i−1), where $1 \leq i \leq L$. Yet according to another embodiment of the present invention, dRR(i)=RR(i+1)−RR(i), where $0 \leq i \leq L-1$. Obviously, in both cases, the length of dRR series is one less than that of the RR series. In the following description, we use the definition dRR(i)=RR(i)−RR(i−1) for illustration purpose, although it shall be understood that the same principles also apply to the other dRR definition.

According to this invention, the RdR plot is constructed by plotting the RR series against the dRR series. The number of data points in the RdR plot equals to the length of the dRR series (e.g., L). Each data point in the RdR plot represents one pair of RR interval and the corresponding dRR interval. In a typical embodiment, {RR(i)} are plotted along the x-axis, and {dRR(i)} are plotted along the y-axis. In another embodiment, {RR(i)} are plotted along the y-axis, and {dRR(i)} are plotted along the x-axis.

Figure 3A:
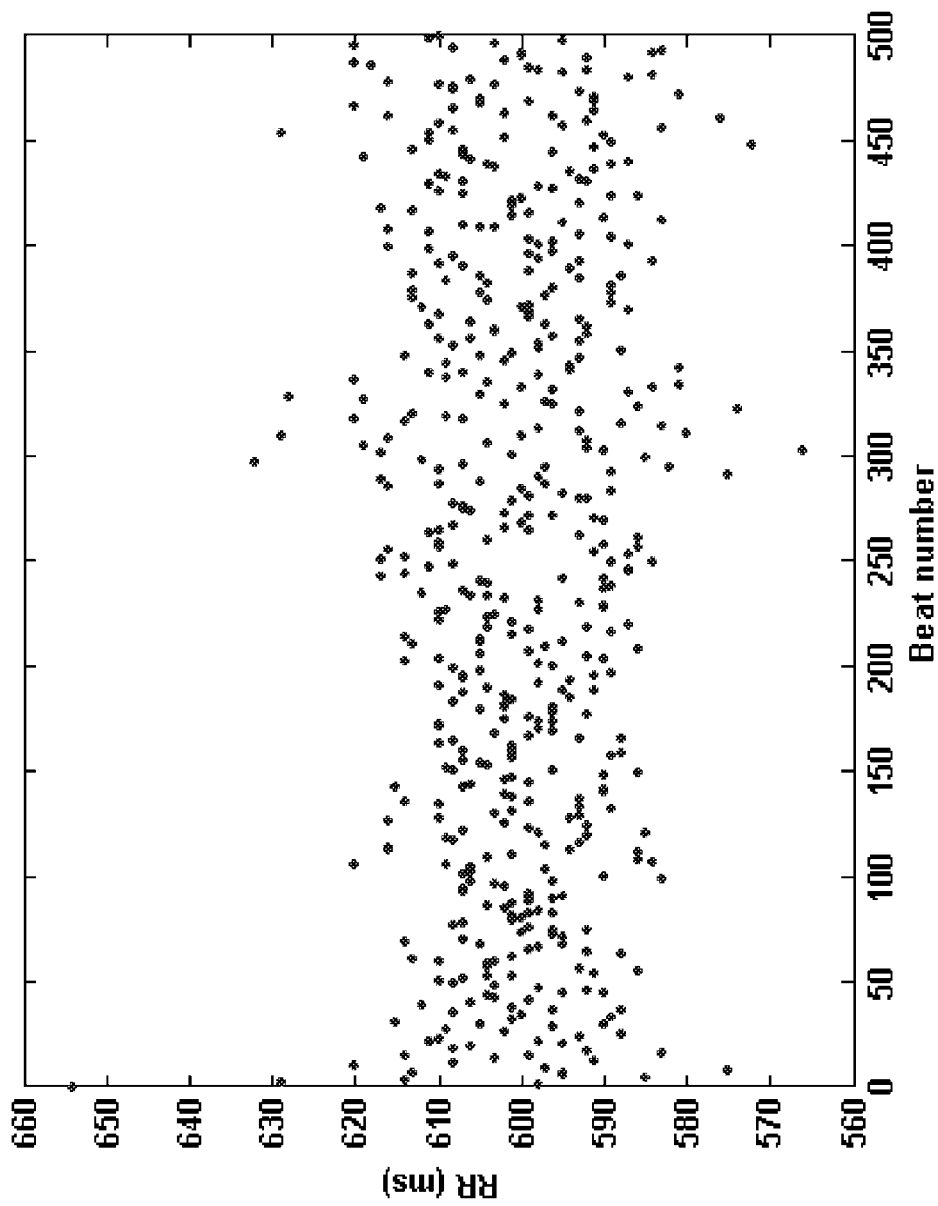
FIG. 3a shows an exemplary tachogram of 500 RR intervals in normal sinus rhythm.
Figure 3B:
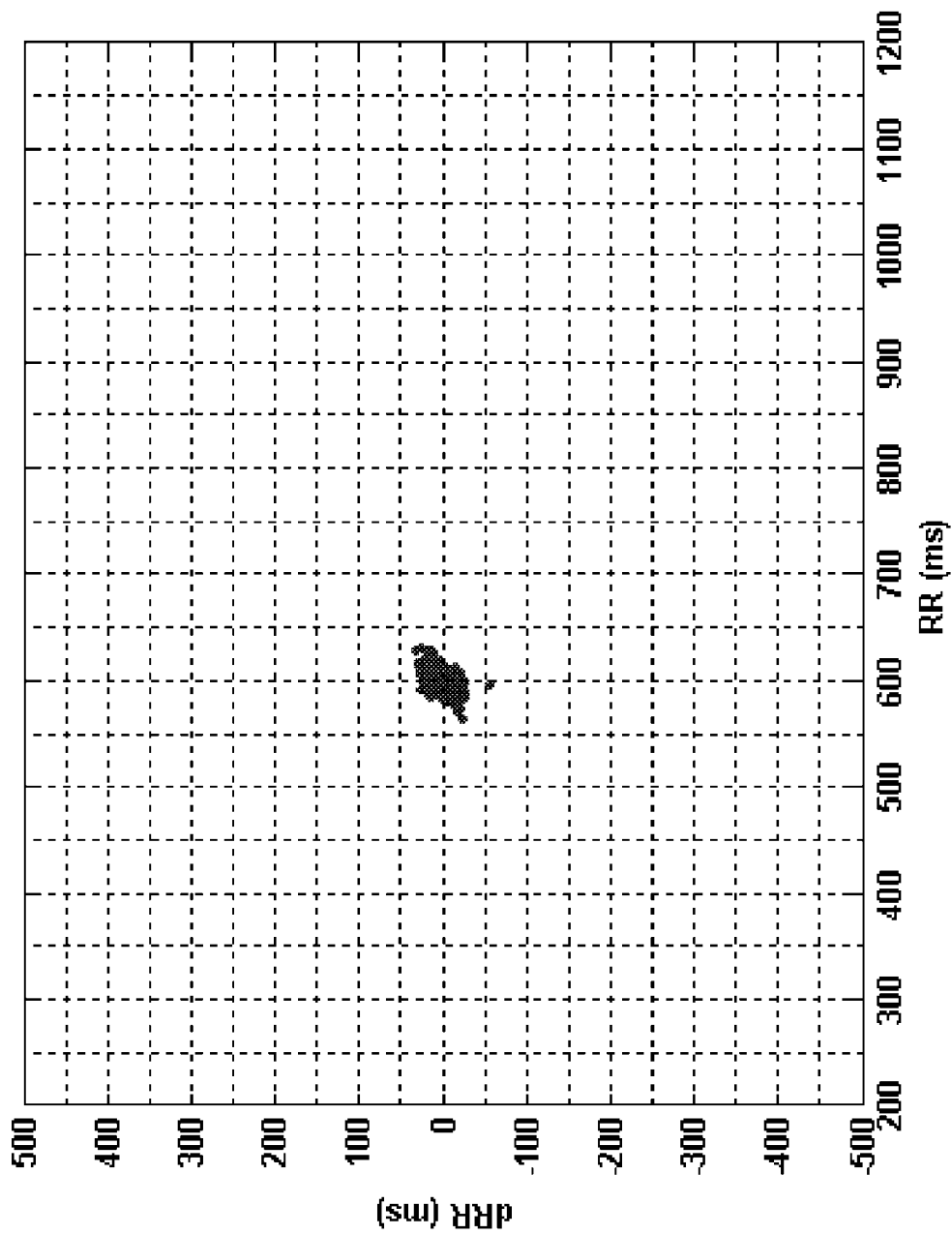
FIG. 3b shows its corresponding RdR plot.
Figure 4A:
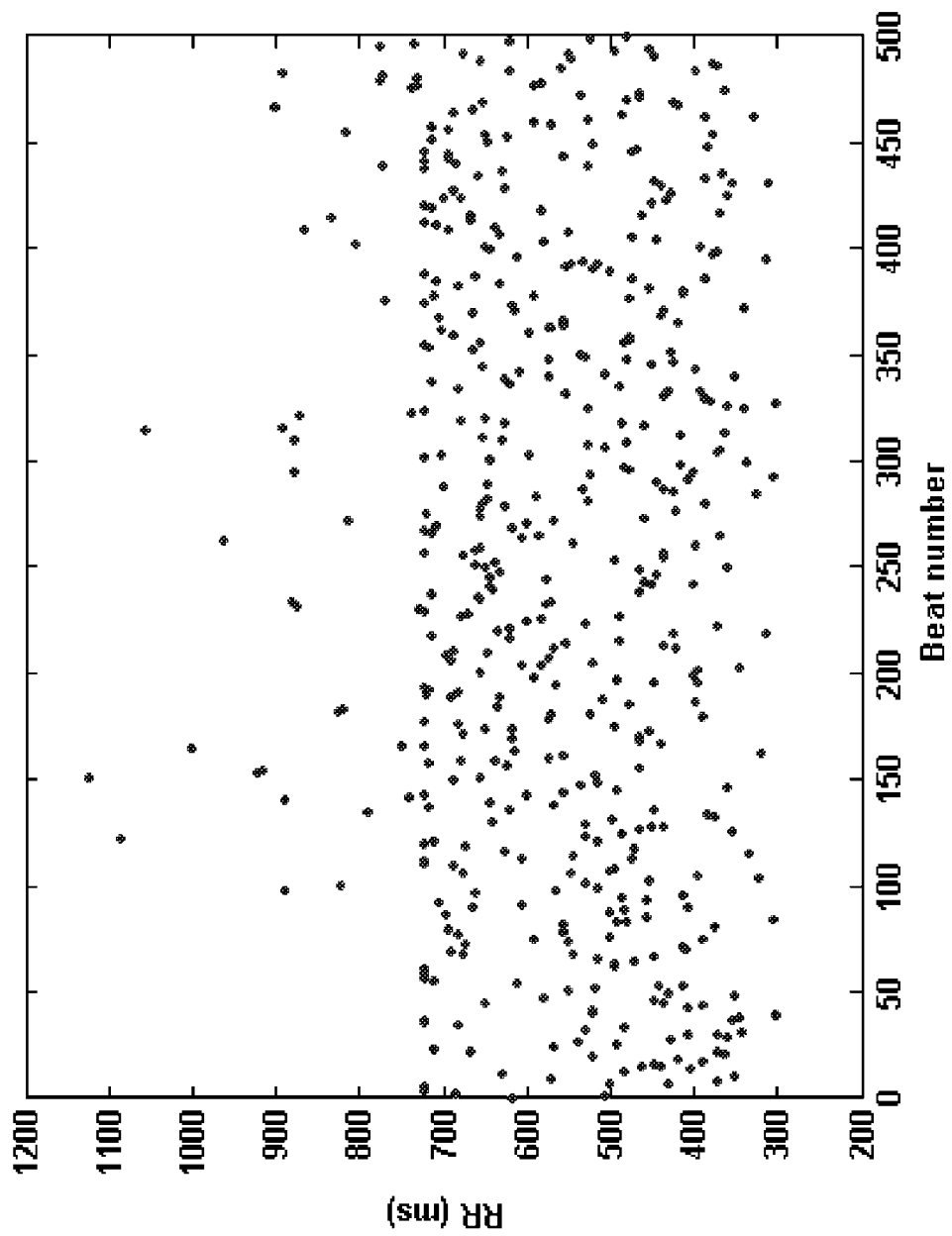
FIG. 4a shows an exemplary tachogram of 500 RR intervals in AF rhythm.
Figure 4B:
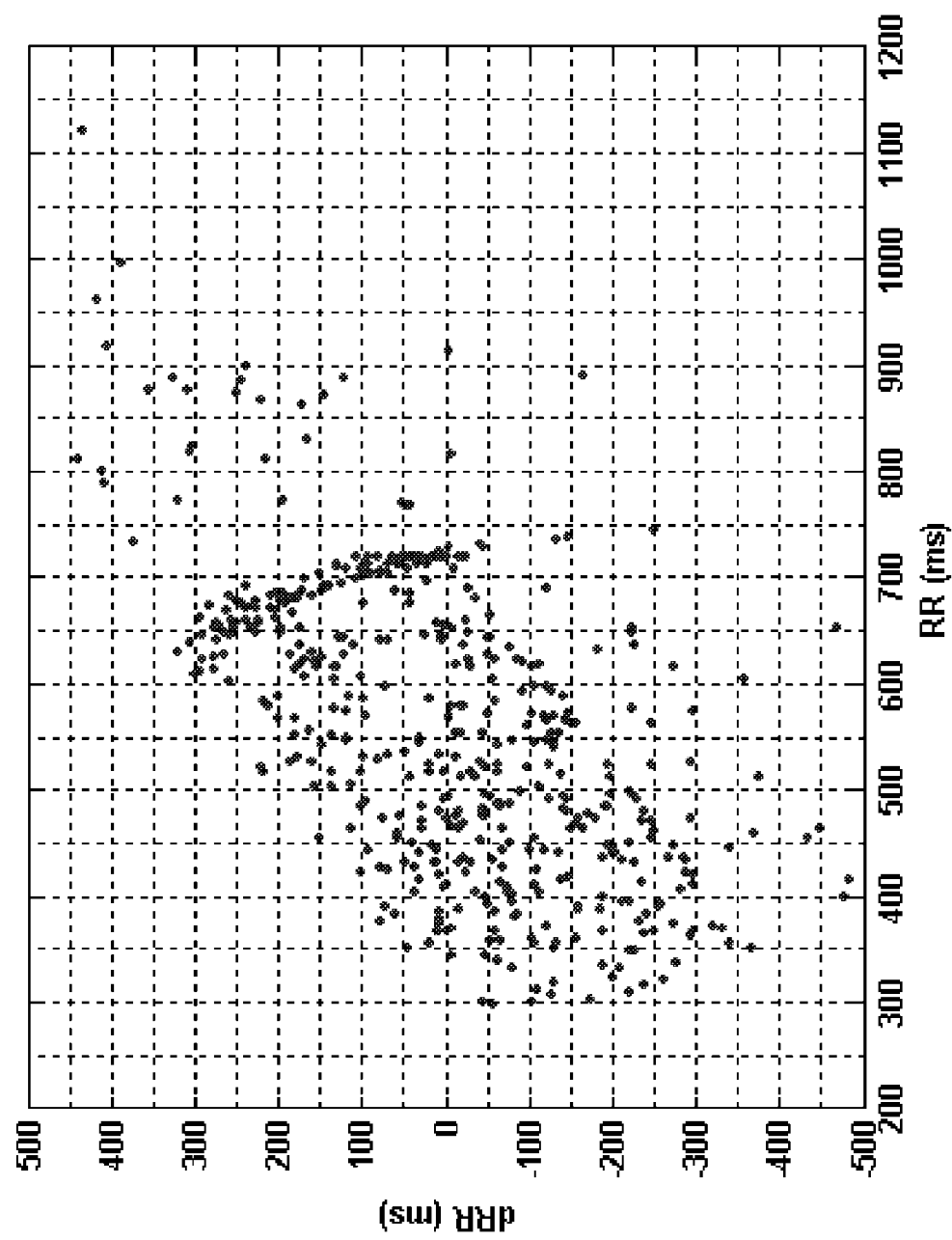
FIG. 4b shows its corresponding RdR plot.

FIG. 3(a) shows an exemplary tachogram of 500 RR intervals in normal sinus rhythm with normal degree of heart rate variability. The corresponding RdR plot is shown in FIG. 3(b). The data points are concentrated in a small region of the 2D plot, indicating the stability of both RR intervals and the dRR intervals. In comparison, FIG. 4a shows an exemplary tachogram of 500 RR intervals in AF rhythm and its corresponding RdR plot is shown in FIG. 4b. The data points are scattered in a large area of the 2D plot, suggesting the irregularity of both the RR intervals and the dRR intervals. Also note that in both FIG. 3(b) and FIG. 4b, the distribution of the data points is oriented from the lower left corner to the upper right corner of the RdR plot. In other words, if applying a linear regression to these data points, the slope of the regression line will be greater than 0 degree but less than 90 degree. This is because larger RR intervals tend to have positive dRR intervals, according to the definition dRR(i)=RR(i)−RR(i−1). On the other hand, if using another definition dRR(i)=RR(i+1)−RR(i), the distribution of the data points will be oriented from the lower right corner to the upper left corner of the RdR plot. As emphasized above, in the following description, we use the first dRR definition for illustration purpose, although it shall be understood that the same principles also apply to the second dRR definition.

Figure 5A:
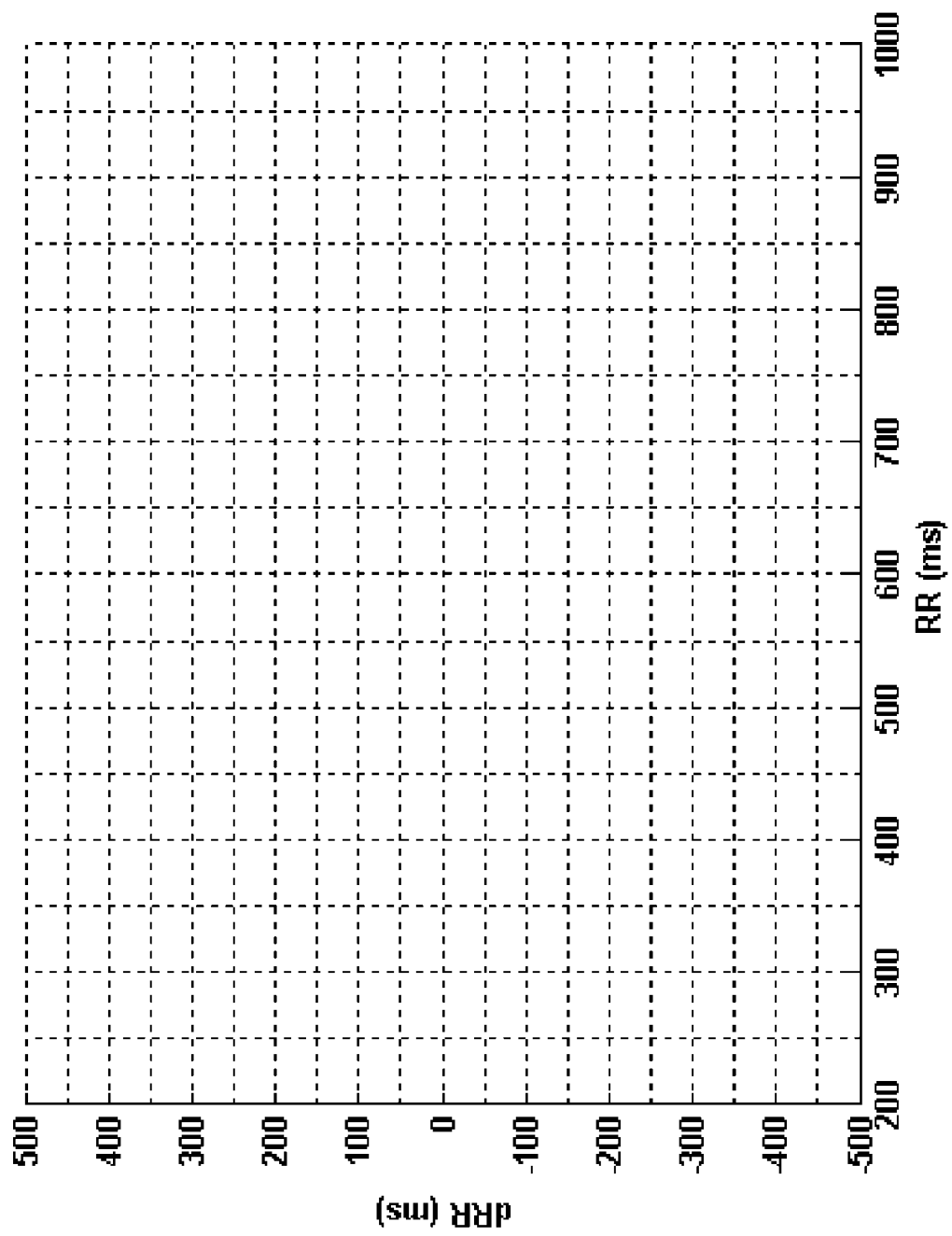
FIG. 5a shows one typical uniform 2D grid.

According to this invention, the RdR plot area is divided by a 2D grid. In a typical embodiment, the 2D grid is equally spaced along both RR axis and dRR axis. Preferably, the grid width for both the RR axis and the dRR axis are set to 50 ms, but each of these two parameters can be independently changed to other values through the external programming device. FIG. 5a shows one typical example, where the RR axis is divided by vertical grid lines at 200 ms, 250 ms, . . . , 1000 ms, and the dRR axis is divided by horizontal grid lines at −500 ms, −450 ms, 500 ms.

Figure 5B:
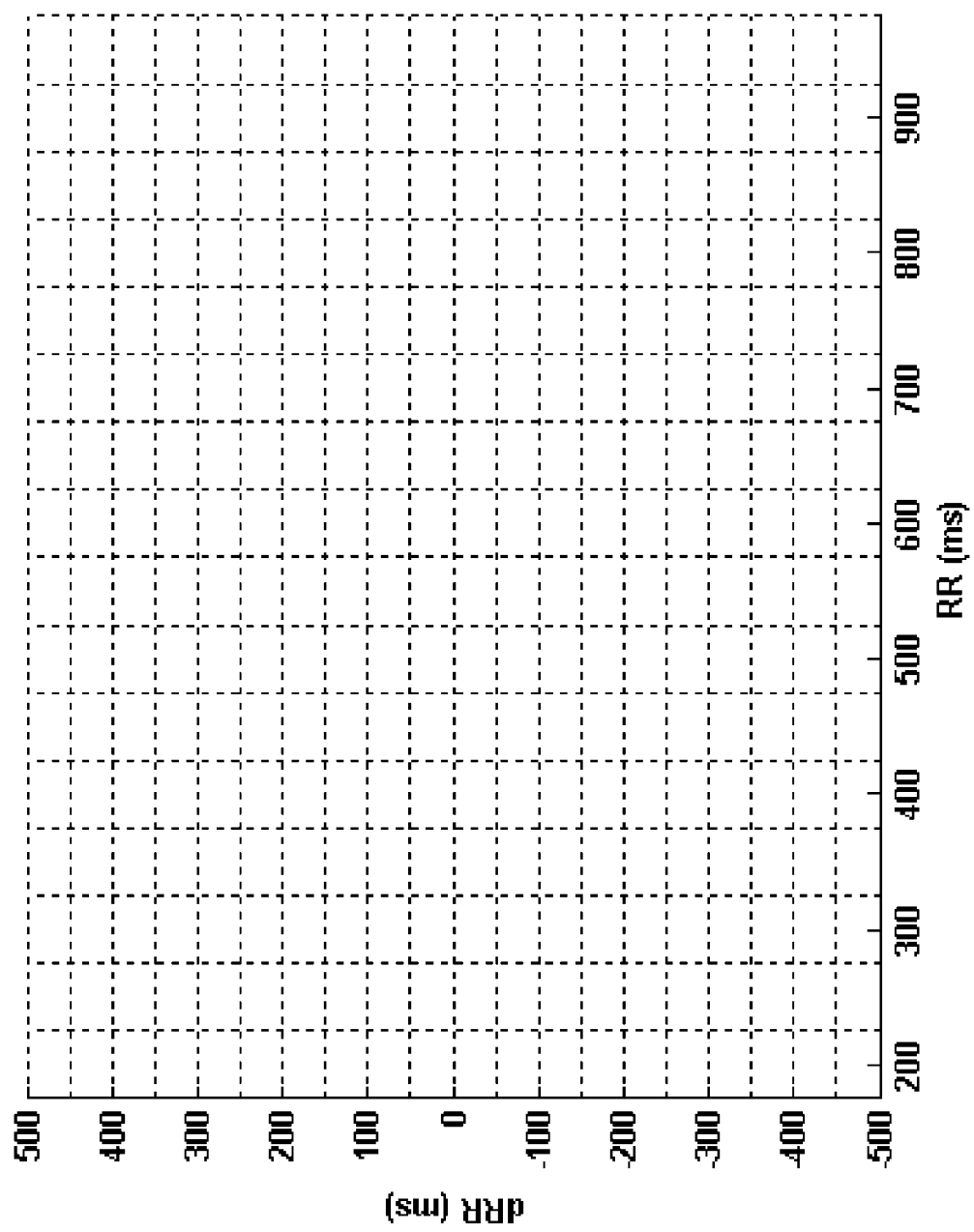
FIG. 5b shows another uniform 2D grid.
Figure 5C:
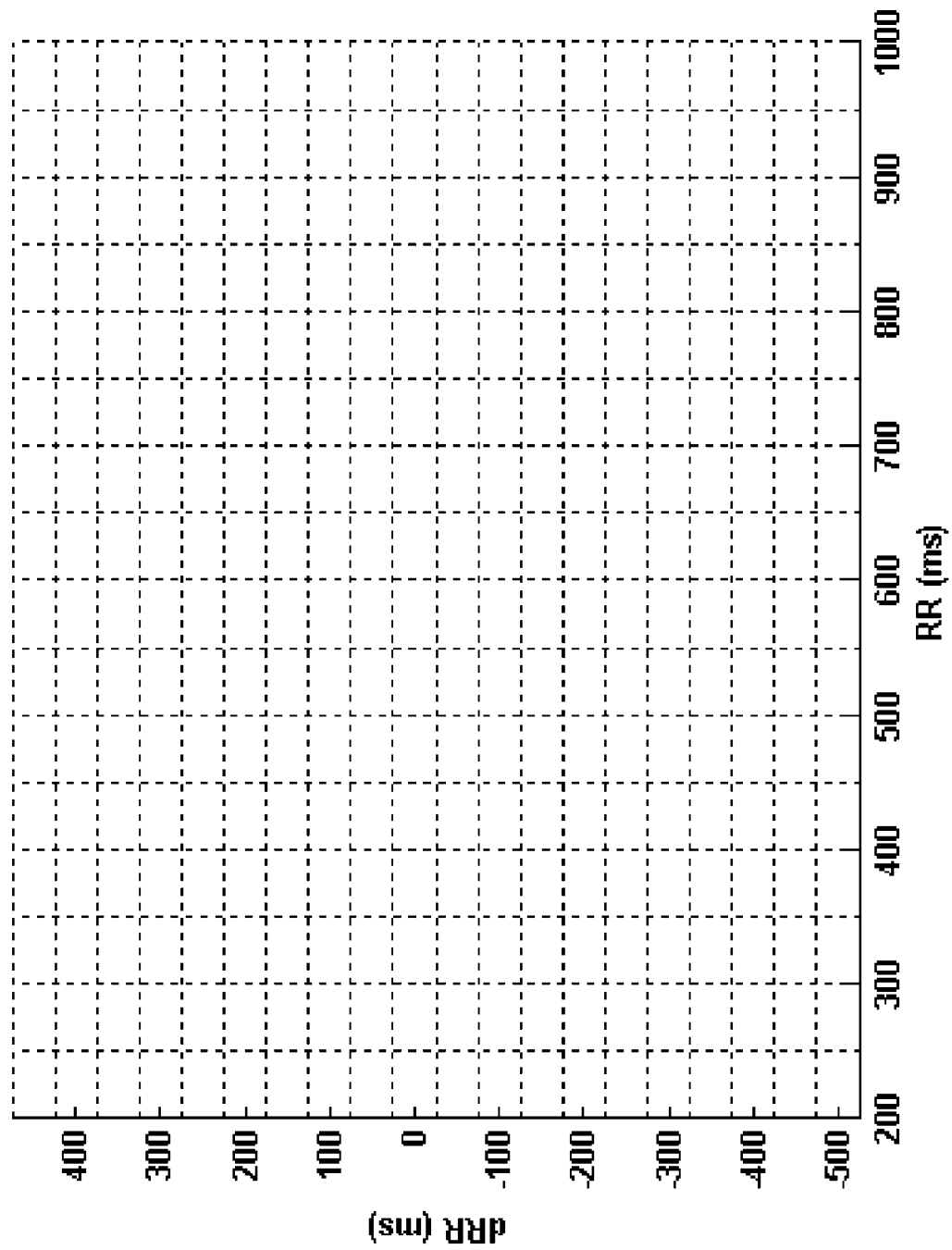
FIG. 5c shows a third uniform 2D grid.
Figure 5D:
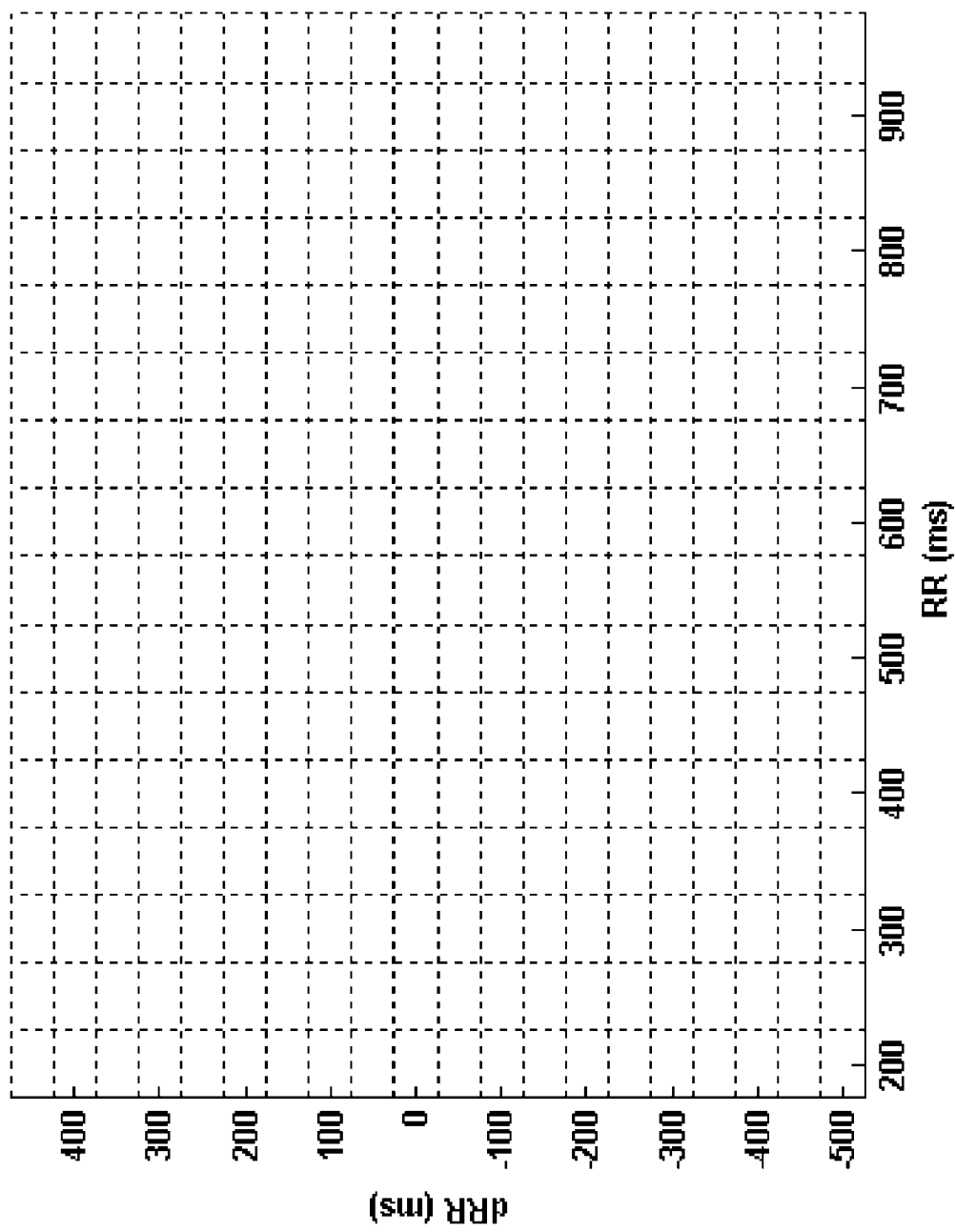
FIG. 5d shows a fourth uniform 2D grid.

FIG. 5b shows another uniform 2D grid that is almost identical to the one shown in FIG. 5a, except that the vertical grid lines are all shifted leftward by 25 ms, i.e., 175 ms, 225 ms, . . . , 975 ms. FIG. 5c shows yet a third uniform 2D grid that is almost identical to the one shown in FIG. 5a, except that the horizontal grid lines are all shifted downward by 25 ms, i.e., −525 ms, −475 ms, . . . , 475 ms. FIG. 5d shows yet a fourth uniform 2D grid that is almost identical to the one shown in FIG. 5d, except that both the horizontal lines and the vertical lines are shifted (respectively leftward and downward) by 25 ms.

Figure 5E:
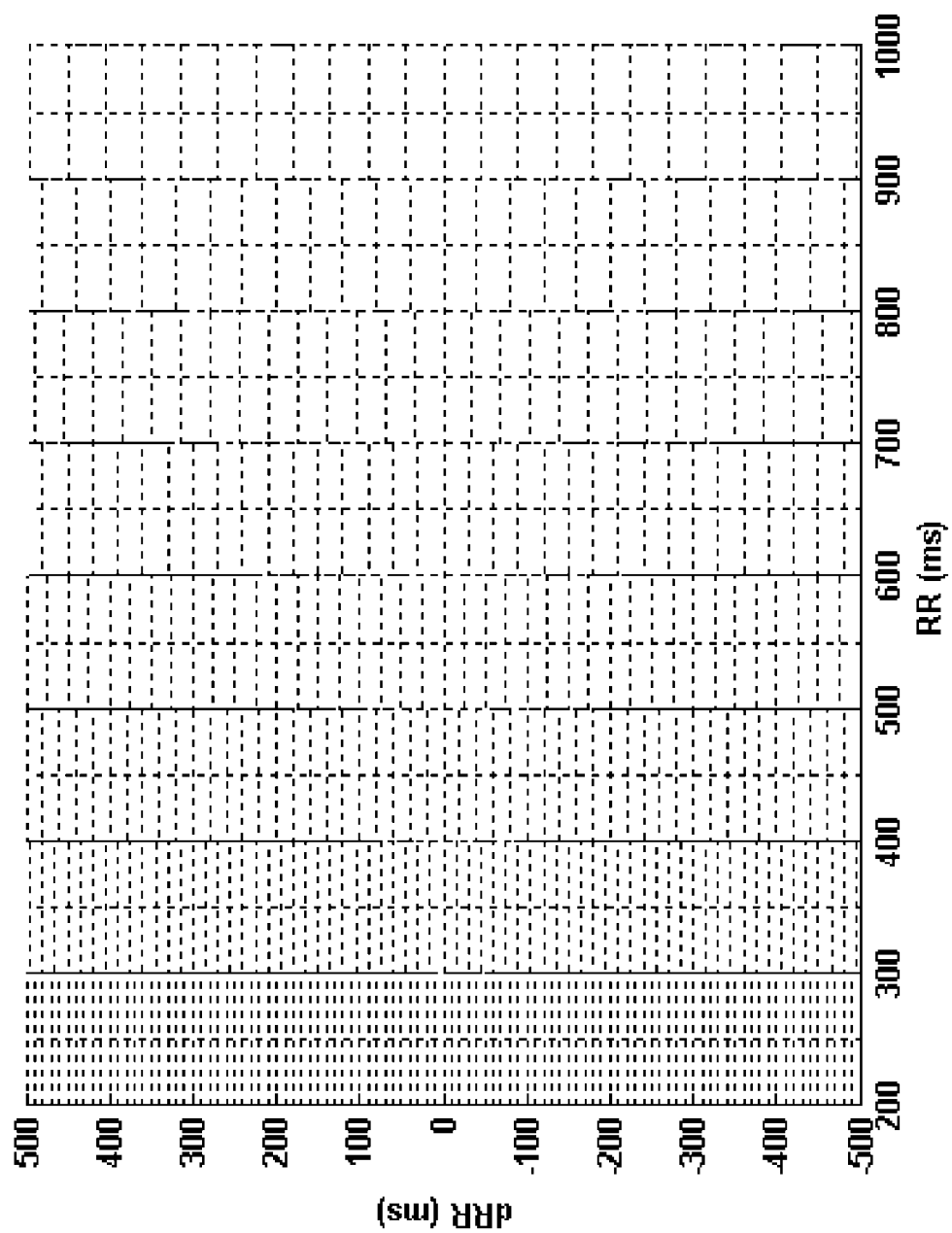
FIG. 5e shows a non-uniform 2D grid.

Yet according to another embodiment of the present invention, the 2D grid is non-uniformly spaced. The grid width can be variable in only RR axis, or only dRR axis, or both. As an example, FIG. 5e shows a gird that is equally spaced in the RR axis but has variable width in the dRR axis. In this example, the grid width for the RR axis is still fixed at 50 ms. The grid width for the dRR axis is set to 10 ms for RR≦200 ms, and is increased by 5 ms for each 100 ms increase of RR interval (i.e., 15 ms for 200 ms<RR≦300 ms, 20 ms for 300 ms<RR≦400 ms, and so on), until the dRR grid width is 50 ms for RR>1000 ms. By designing this variable dRR grid width, the heart rate dependent RR interval variation (e.g., in normal sinus rhythm, dRR tends to be larger in slower heart rate, but smaller in higher heart rate) is taken into consideration.

In the following description, we use the equally spaced 2D grid shown in FIG. 5a for illustration purpose, although it shall be understood that the same principles also apply to other types of 2D grids including the non-uniform 2D grid.

For illustration purpose, FIGS. 6-13 show some representative examples of RdR plots corresponding to different types of cardiac rhythms. The number of data points shown in each of these RdR plots is 16.

Figure 6:
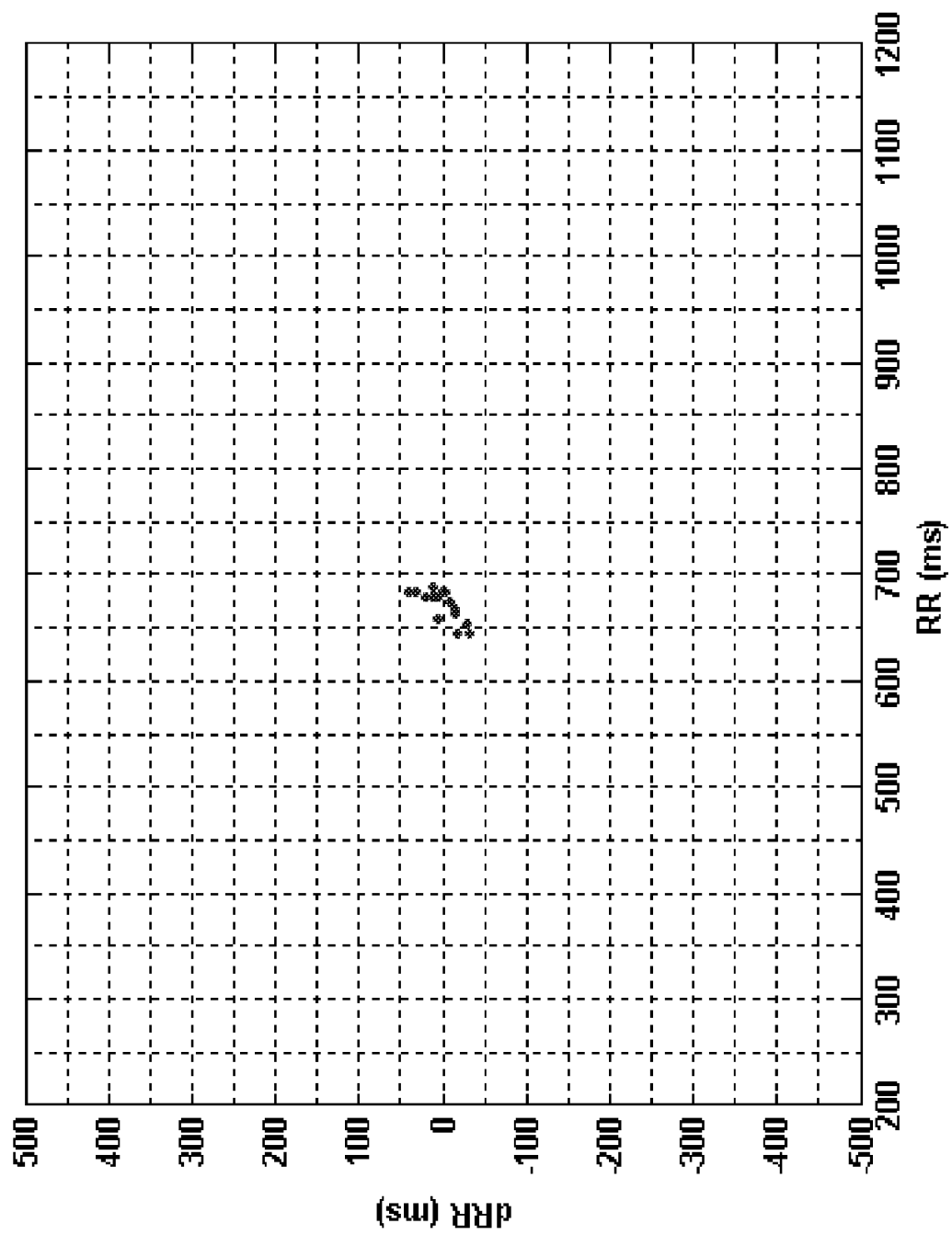
FIG. 6 shows an exemplary scatter RdR plot of stable normal sinus rhythm.

FIG. 6 shows an exemplary scatter RdR plot of stable normal sinus rhythm. Similar to FIG. 1(b), the data points are condensed in a small area of the 2D plot, indicating the stability of both RR intervals and the dRR intervals.

Figure 7:
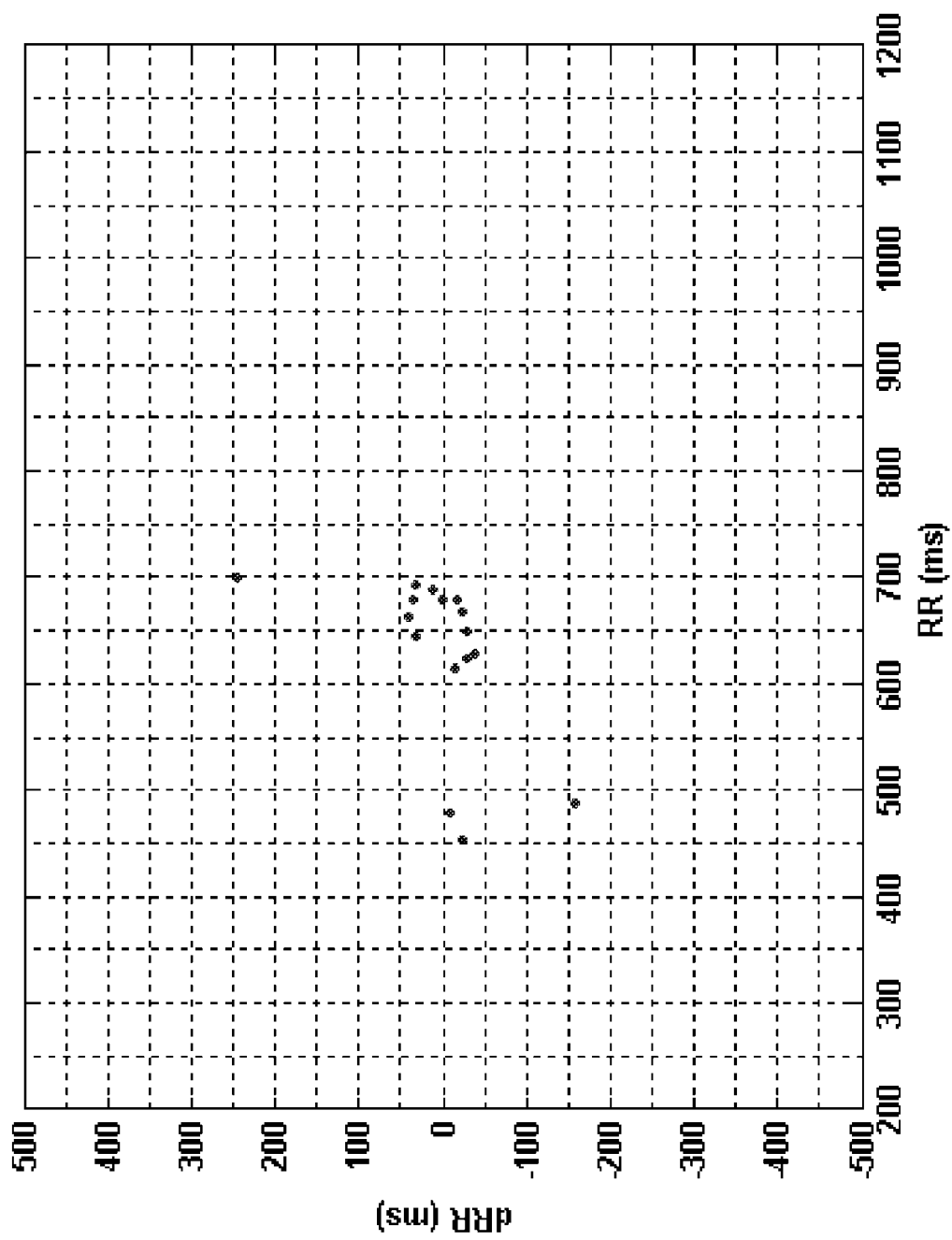
FIG. 7 shows an exemplary scatter RdR plot of sinus rhythm with an extra-systolic triplet.

FIG. 7 shows an exemplary scatter RdR plot of sinus rhythm with an extra-systolic triplet. Most data points are concentrated in a small area of the 2D plot, whereas 4 data points are outliers due to: 3 very short RR intervals of the triplet with large negative dRR of the first extra-systole, and 1 normal RR interval with large positive dRR after the last extra-systole.

Figure 8:
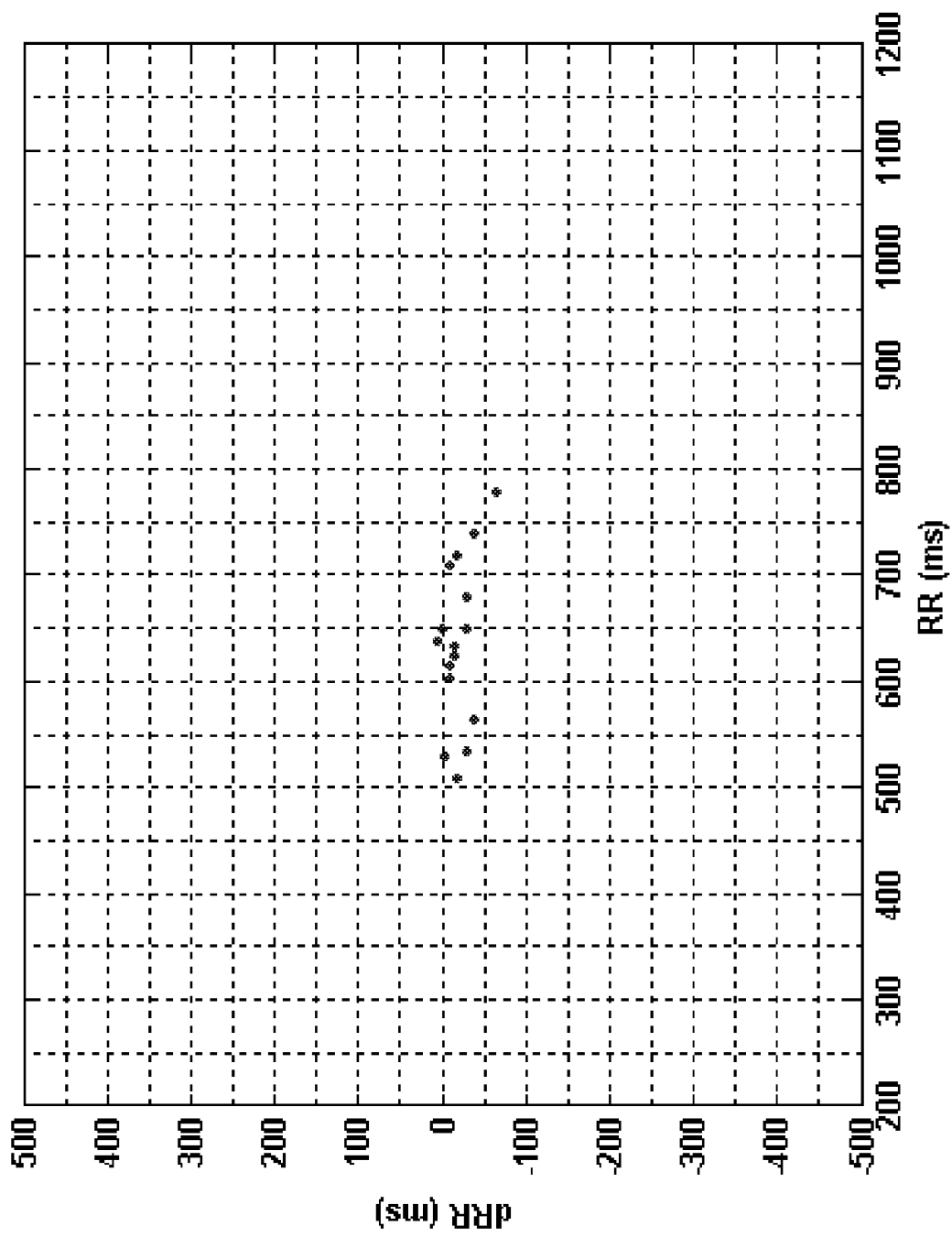
FIG. 8 shows an exemplary scatter RdR plot of sinus rhythm during onset of exercise.

FIG. 8 shows an exemplary scatter RdR plot of sinus rhythm during onset of exercise. The increase of heart rate is associated with shortening of RR intervals, whereas the change of heart rate is gradual as evidenced by limited range of dRR (mostly negative).

Figure 9:
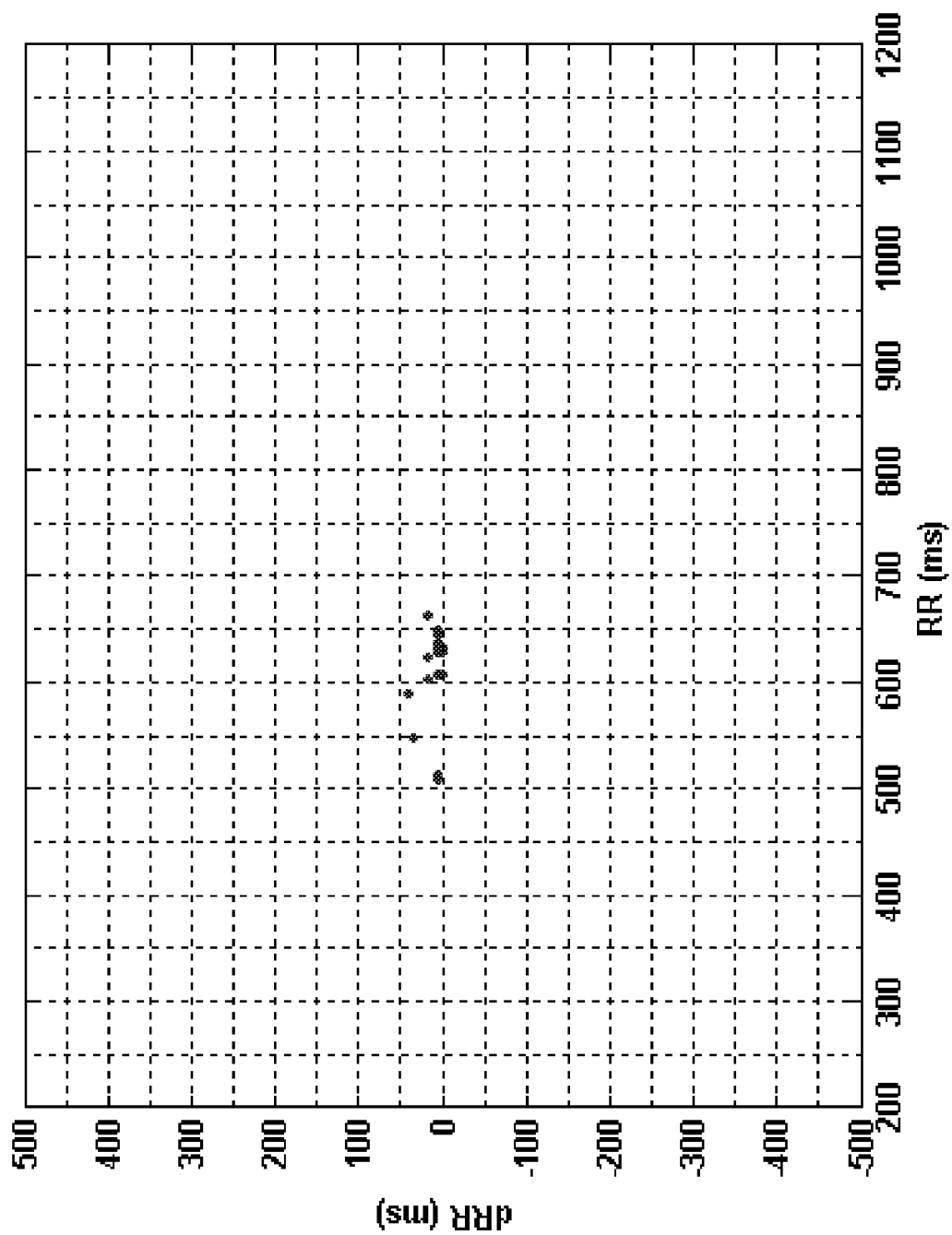
FIG. 9 shows an exemplary scatter RdR plot of sinus rhythm during exercise recovery period.

FIG. 9 shows an exemplary scatter RdR plot of sinus rhythm during exercise recovery period. The decrease of heart rate is associated with lengthening of RR intervals, whereas the change of heart rate is gradual as evidenced by limited range of dRR (mostly positive).

Figure 10:
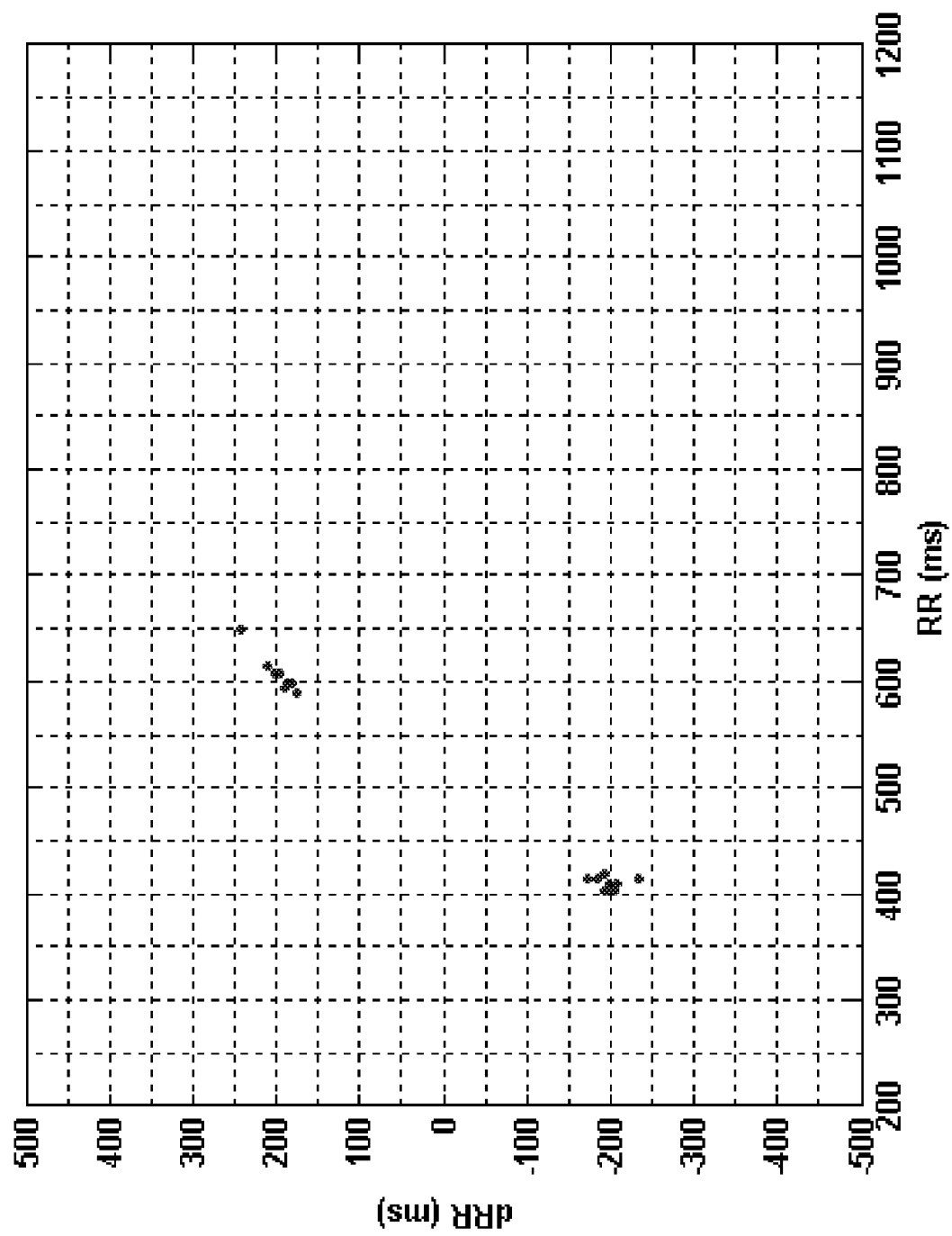
FIG. 10 shows an exemplary scatter RdR plot of bigeminy rhythm.

FIG. 10 shows an exemplary scatter RdR plot of bigeminy rhythm. Such pattern of RR intervals (repetitive short-long sequence) could be caused by pathological conditions such as frequent extra-systoles, or due to device sensing problems, such as T wave over-sensing. The scatter RdR plot is characterized by two separate yet condensed clusters of data points, respectively located in the upper right and lower left areas.

Figure 11:
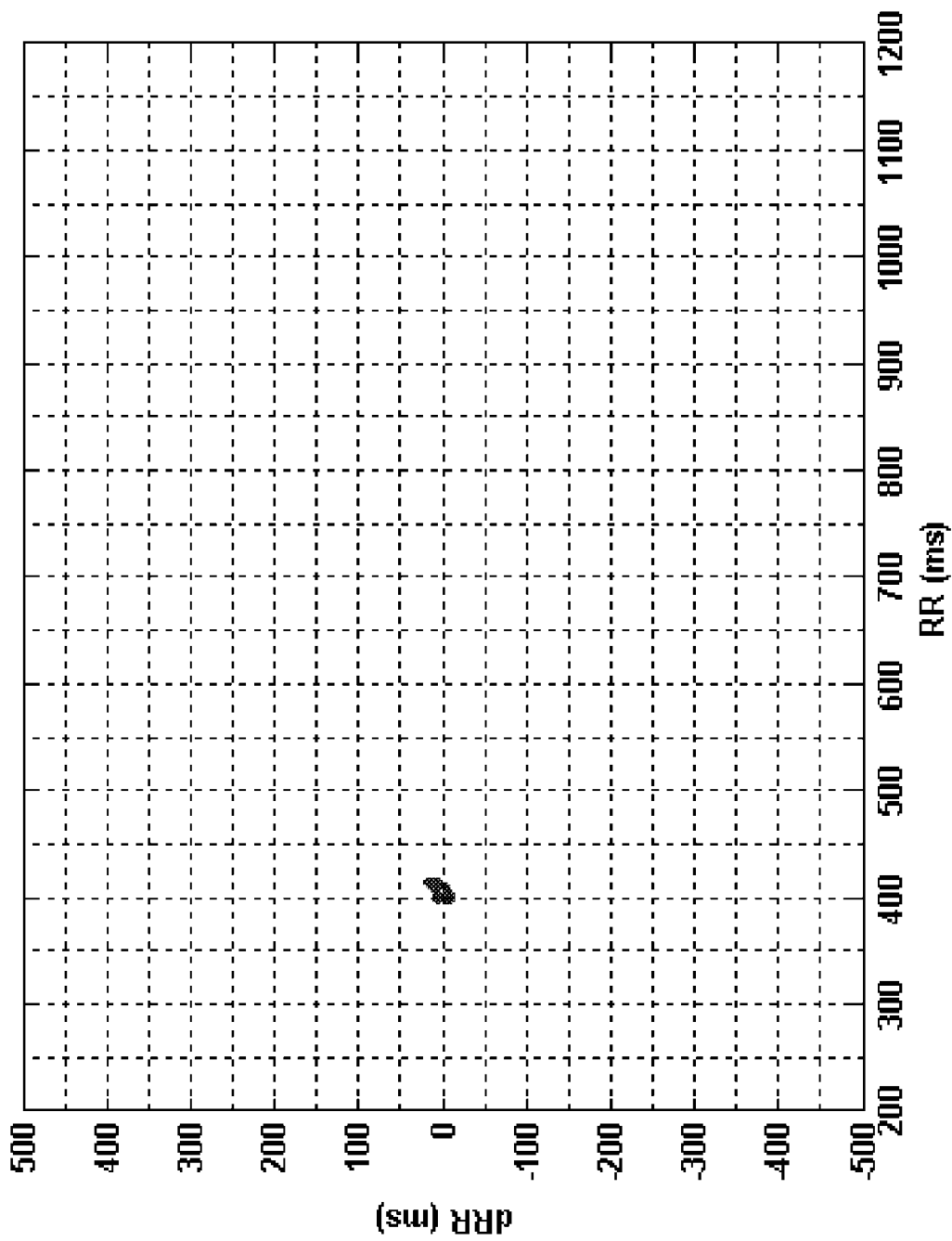
FIG. 11 shows an exemplary scatter RdR plot of stable sinus tachycardia rhythm.

FIG. 11 shows an exemplary scatter RdR plot of stable sinus tachycardia rhythm. The data points are concentrated in a small area of the RdR plot. Compared to the normal sinus rhythm (FIG. 6), the data points are even more condensed (smaller dRR intervals), and the cluster is shifted further to the left (shorter RR intervals). Similar patterns of scatter RdR plot are also applicable to other stable supra-ventricular tachycardia such as AV nodal reentrant tachycardia, or stable ventricular tachycardia.

Figure 12:
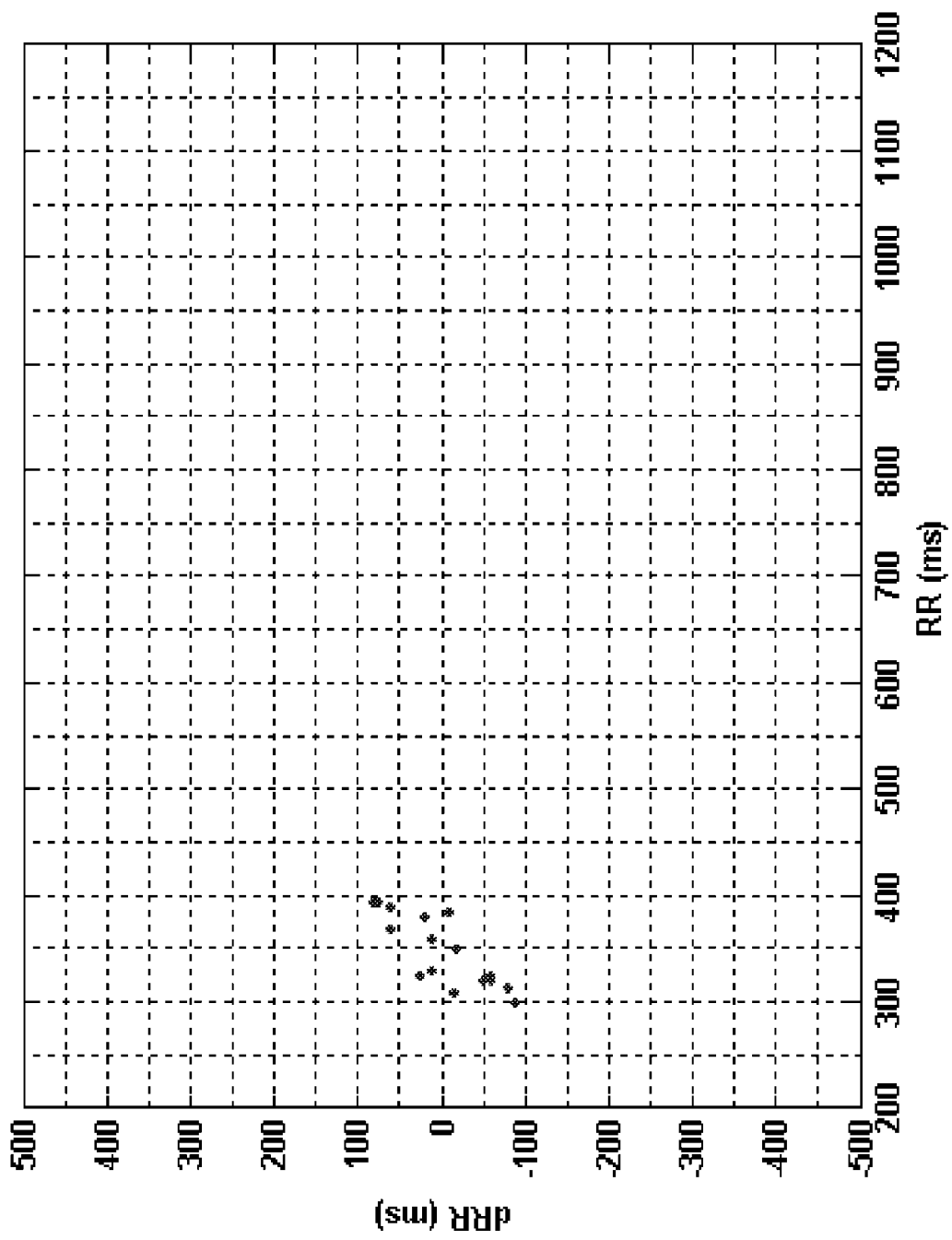
FIG. 12 shows an exemplary scatter RdR plot of VF rhythm.

FIG. 12 shows an exemplary scatter RdR plot of VF rhythm. The data points are located in the left of the RdR plot indicating high ventricular rate, and the data points are distributed in a large area indicating irregularity of the ventricular rhythm.

Figure 13:
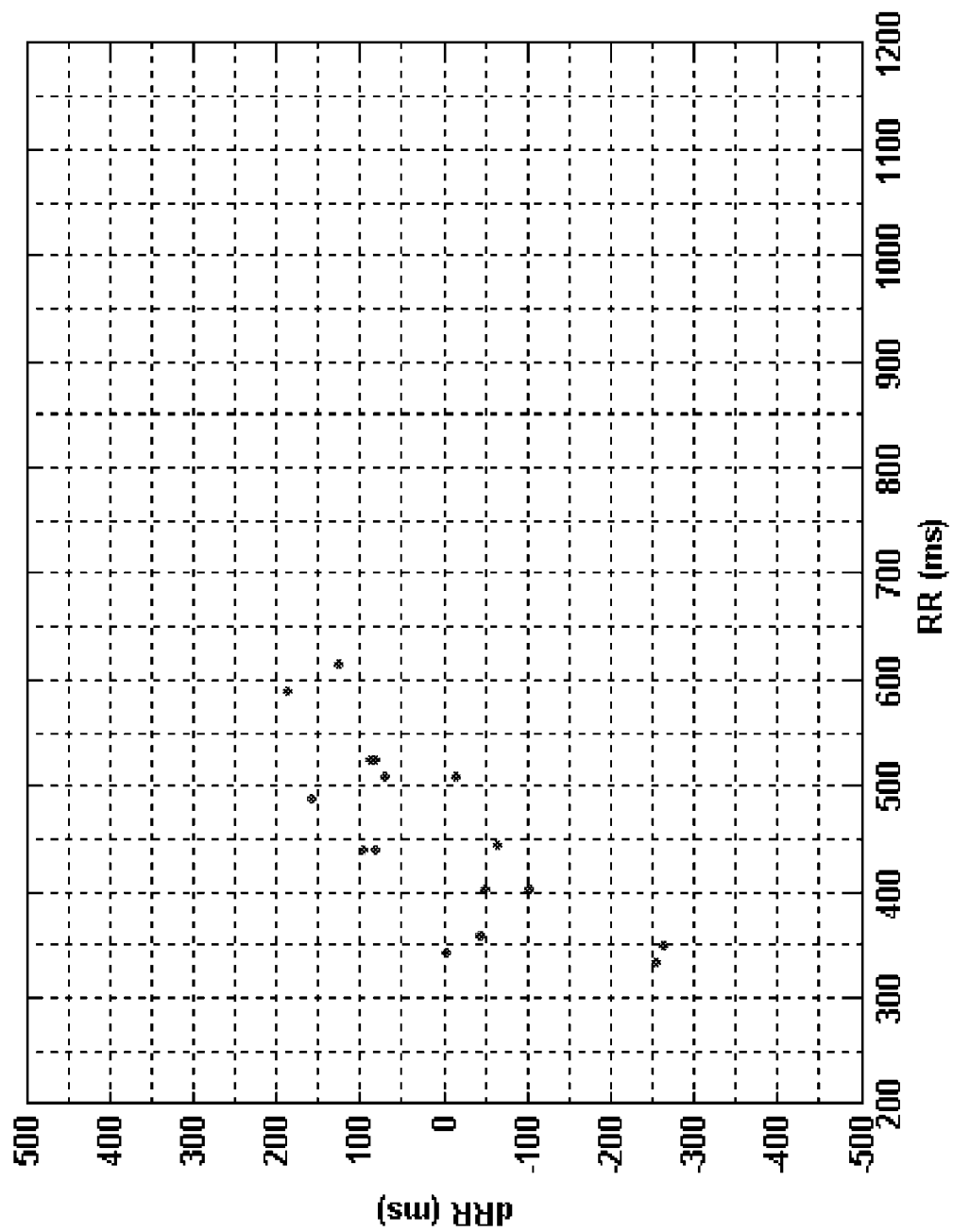
FIG. 13 shows an exemplary scatter RdR plot of AF rhythm.

FIG. 13 shows an exemplary scatter RdR plot of AF rhythm. Similar to FIG. 4b, the data points are scattered in a large area of the RdR plot, suggesting the irregularity of both the RR intervals and the dRR intervals. Compared to the VF rhythm (FIG. 12), the data points are even more scattered (larger dRR intervals), and the distribution is shifted to the right (more longer RR intervals due to non-conducted AF impulses).

Clearly, various types of cardiac rhythms show different characteristic clustering patterns in the RdR plot. The RdR plot is advantageous than the conventional Lorenz plot (either based on RR intervals or dRR intervals) in that it embeds both RR intervals and dRR intervals in the same plot. From the RdR plot, both the heart rate (RR intervals) and change of heart rate (dRR intervals) are readily available, thus offering more information for cardiac rhythm classification.

It is clear that the change of heart rate (dRR intervals) corresponds to the first derivative of the RR intervals. Therefore, the acceleration or deceleration of the heart rate, which corresponds to the second derivative of the RR intervals, can also be derived from the change of dRR intervals (i.e., first derivative of the dRR intervals). The information on heart rate, change of heart rate, and heart rate acceleration/deceleration can all be obtained from the RdR plot, by adding trajectory which connects the scattered data points in sequence. In other words, point 1 (RR(1), dRR(1)) is connected to point 2 (RR(2), dRR(2)), which is connected to point 3 (RR(3), dRR(3)), and so on.

Figure 14:
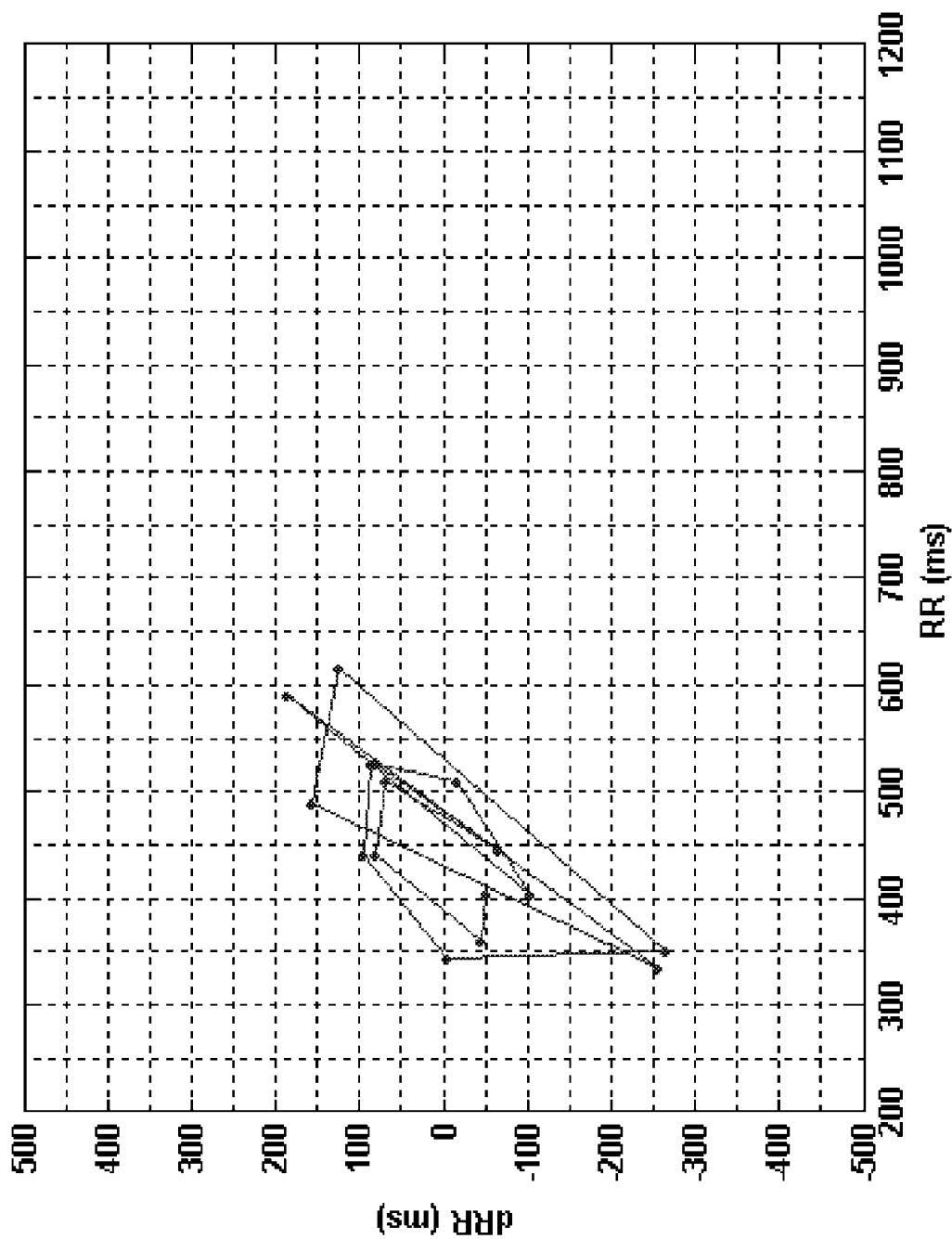
FIG. 14 shows the same RdR plot of FIG. 13 with added trajectory.

As an example, FIG. 14 shows the same RdR plot of FIG. 13 with added trajectory. For each pair of two adjacent data points connected by a trajectory line, their horizontal distance (along RR axis) is the change of RR interval (e.g., RR(i+1)−RR(i)), which is already represented by the dRR interval of the second data point. On the other hand, their vertical distance (along dRR axis)
is the change of dRR interval (e.g., dRR(i+1)−dRR(i)), which represents the acceleration or deceleration of the heart rate within the corresponding three RR intervals.

Because different cardiac rhythms show distinctive patterns of clustering in the RdR plots, cardiac rhythm classification can be achieved by conventional pattern recognition techniques, such as neural network, fuzzy logic, etc., as known in the art. Numerous features can be extracted from the RdR plot to quantify the data clustering patterns. Some representative features include, but are not limited to the following metrics:

Count of non-zero cells (NZCEL), which is defined as the total number of RdR grid cells that have at least one data point. Clearly, NZCEL is smaller for a denser RdR plot (e.g., normal sinus rhythm or stable sinus tachycardia), and is larger for a sparser RdR plot (e.g., AF or VF). For instance, using the grid as defined in FIG. 5a, the NZCEL metrics for the examples shown in FIGS. 6-13 are respectively: 3, 7, 8, 4, 6, 2, 6, 13.

Count of non-zero columns (NZCOL), which is defined as the total number of RdR grid columns that have at least one data point. Clearly, NZCOL is smaller when RR intervals are limited with a narrow range (e.g., normal sinus rhythm, or stable sinus tachycardia, or VF of very short RR intervals), and is larger when RR intervals are stretched (e.g., AF, or onset/offset of exercise). For instance, using the grid as defined in FIG. 5a, the NZCOL metrics for the examples shown in FIGS. 6-13 are respectively: 2, 4, 6, 4, 4, 1, 2, 7.

Count of non-zero rows (NZROW), which is defined as the total number of RdR grid rows that have at least one data point. Clearly, NZROW is smaller when dRR intervals are limited with a narrow range (e.g., normal sinus rhythm, or stable sinus tachycardia, or onset/offset of exercise due to gradual change of heart rate), and is larger when dRR intervals are stretched (e.g., AF). For instance, using the grid as defined in FIG. 5a, the NZROW metrics for the examples shown in FIGS. 6-13 are respectively: 2, 4, 3, 1, 4, 2, 4, 7.

Count of local peaks (NPEAK), which is defined as the total number of local peaks in the RdR plot. According to a preferred embodiment, a grid cell is a local peak if (a) the number of data points within this cell equals to or exceeds a predefined or user-programmable threshold, and (b) the number of data points within this cell is greater than that of any of its eight adjacent grid cells. In a typical embodiment, the threshold is set to 25% of the total data count. For example, the threshold is set to 4 for 16 data points. Generally, AF tends to have no local peak whereas other rhythms tend to have 1 or more local peaks. For instance, using the grid as defined in FIG. 5a, the NPEAK metrics for the examples shown in FIGS. 6-13 are respectively: 1, 1, 1, 1, 1, 1, 2, 0.

Total trajectory distance along RR axis (XDIST), which is defined as the total trajectory distance along the RR axis for all data points. According to one embodiment of the present invention, for two data points connected by a trajectory line, their trajectory distance along the RR axis is the absolute difference between their RR intervals. According to another embodiment of the present invention, for two data points connected by a trajectory line, their trajectory distance along the RR axis is the absolute difference between their grid column numbers. Generally, unstable rhythms (e.g. AF, bigeminy, frequent ectopies) tend to have larger XDIST than stable rhythms. For instance, using the grid as defined in FIG. 5a, the XDIST metrics (in terms of grid columns) for the examples shown in FIGS. 6-13 are respectively: 3, 13, 5, 3, 59, 0, 9, 34.

Total trajectory distance along dRR axis (YDIST), which is defined as the total trajectory distance along the dRR axis for all data points. According to one embodiment of the present invention, for two data points connected by a trajectory line, their trajectory distance along the dRR axis is the absolute difference between their dRR intervals. According to another embodiment of the present invention, for two data points connected by a trajectory line, their trajectory distance along the dRR axis is the absolute difference between their grid row numbers. Generally, unstable rhythms (e.g. AF, bigeminy, frequent ectopies) tend to have larger YDIST than stable rhythms. For instance, using the grid as defined in FIG. 5a, the YDIST metrics (in terms of grid rows) for the examples shown in FIGS. 6-13 are respectively: 11, 21, 5, 0, 116, 8, 27, 52.

Distance to global center (DGMAX), which is defined as the total distance from all data points to the global center. According to this invention, the global center is the grid cell that has the most data points. The distance from one data point to another is the sum of their horizontal distance (along RR axis) and their vertical distance (along dRR axis). In one embodiment, the distance is measured in terms of absolute time intervals (e.g., ms unit). In other embodiment, the distance is measured in terms of grid count (e.g., number of columns plus number of rows). Generally, DGMAX is larger for AF and bigeminy than other rhythms. For instance, using the grid as defined in FIG. 5a, the DGMAX metrics (in terms of grid count) for the examples shown in FIGS. 6-13 are respectively: 10, 33, 22, 8, 93, 7, 32, 62.

Distance to positive center (DPMAX), which is defined as the total distance from all positive data points with dRR≧0 to the positive center. According to this invention, the positive center is the positive grid cell (i.e., dRR≧0) that has the most data points. The distance from one data point to another is the sum of their horizontal distance (along RR axis) and their vertical distance (along dRR axis). In one embodiment, the distance is measured in terms of absolute time intervals (e.g., ms unit). In other embodiment, the distance is measured in terms of grid count (e.g., number of columns plus number of rows). Generally, AF rhythm has larger DPMAX than the bigeminy rhythm. For instance, using the grid as defined in FIG. 5a, the DPMAX metrics (in terms of grid count) for the examples shown in FIGS. 6-13 are respectively: 0, 6, 1, 8, 6, 0, 6, 13.

Distance to negative center (DNMAX), which is defined as the total distance from all negative data points with dRR<0 to the negative center. According to this invention, the negative center is the negative grid cell (i.e., dRR<0) that has the most data points. The distance from one data point to another is the sum of their horizontal distance (along RR axis) and their vertical distance (along dRR axis). In one embodiment, the distance is measured in terms of absolute time intervals (e.g., ms unit). In other embodiments, the distance is measured in terms of grid count (e.g., number of columns plus number of rows). Generally, AF rhythm has larger DNMAX than the bigeminy rhythm. For instance, using the grid as defined in FIG. 5a, the DNMAX metrics (in terms of grid count) for the examples shown in FIGS. 6-13 are respectively: 2, 15, 19, 0, 3, 0, 6, 39.

The metrics listed above respectively characterize different aspects of the data clustering patterns in the RdR plot. Accordingly, different cardiac rhythms can be separated by evaluating one or more of these metrics, or the combinations of multiple metrics. For example, AF is indicated by large NZCEL, large NZROW, large NZCOL, small NPEAK, large XDIST, large YDIST, large DGMAX, large DPMAX, and large DNMAX. The AF detection is made by comparing one or more metrics with respective threshold values that are predefined or user-programmable. As known in the art, the optimal threshold values, as well as the optimal decision tree to classify different cardiac rhythms can be pre-determined (e.g., based on sensitivity/specificity analysis) by evaluating in a training RR interval database with known rhythm classifications.

Yet according to another embodiment of the present invention, the metrics described above are calculated for multiple 2D grids, and then they are pooled together for rhythm classification. In an exemplary embodiment, the metrics are first calculated based on the 2D grid shown in FIG. 5a, then calculated based on the 2D grid shown in FIG. 5b, then further calculated based on the 2D grid shown in FIG. 5c, and finally calculated based on the 2D grid shown in FIG. 5d. Due to the limited grid resolution (50 ms in above examples), a cluster of data points may be all located in the same grid cell according to one 2D grid, but may be assigned to two or more adjacent grid cells according to another 2D grid. Therefore, the metric variance due to grid resolution could be minimized by calculating the metrics using different 2D grids, by shifting the grid lines horizontally, vertically, or both. The metrics obtained with these 2D grids could be pooled together by different methods, including but are not limited to, calculating their mean, median, minimum, maximum, sum, product, etc.

For example, using the grid as defined in FIG. 5a, the NZCEL metrics for the examples shown in FIGS. 6-13 are respectively: 3, 7, 8, 4, 6, 2, 6, 13. Using the grid as defined in FIG. 5b, the NZCEL metrics for the examples shown in FIGS. 6-13 are respectively: 4, 9, 8, 4, 5, 2, 9, 12. Using the grid as defined in FIG. 5c, the NZCEL metrics for the examples shown in FIGS. 6-13 are respectively: 5, 9, 9, 4, 6, 1, 7, 13. Using the grid as defined in FIG. 5d, the NZCEL metrics for the examples shown in FIGS. 6-13 are respectively: 4, 10, 10, 5, 5, 1, 9, 13. To pool these data together, the minimum NZCEL (among four 2D grids) for the examples shown in FIGS. 6-13 are respectively: 3, 7, 8, 4, 5, 1, 6, 12. Clearly, for the purpose of AF detection, the minimum NZCEL (among four 2D grids) has more classification power (i.e., to separate AF from other rhythms) than the NZCEL obtained with a single 2D grid.

In another example, using the grid as defined in FIG. 5a, the NPEAK metrics for the examples shown in FIGS. 6-13 are respectively: 1, 1, 1, 1, 1, 1, 2, 0. Using the grid as defined in FIG. 5b, the NPEAK metrics for the examples shown in FIGS. 6-13 are respectively: 1, 2, 0, 1, 2, 1, 0, 0. Using the grid as defined in FIG. 5c, the NPEAK metrics for the examples shown in FIGS. 6-13 are respectively: 1, 1, 1, 1, 2, 1, 1, 0. Using the grid as defined in FIG. 5d, the NPEAK metrics for the examples shown in FIGS. 6-13 are respectively: 1, 0, 1, 1, 2, 1, 0, 0. To pool these data together, the sum NPEAK (of four 2D grids) for the examples shown in FIGS. 6-13 are respectively: 4, 4, 3, 4, 7, 4, 3, 0. Clearly, for the purpose of AF detection, the sum NPEAK (of four 2D grids) has more classification power (i.e., to separate AF from other rhythms) than the NPEAK obtained with a single 2D grid.

Yet according to a further embodiment of the present invention, the metrics described above are calculated for multiple segments of RR intervals. Preliminary rhythm classification is made within each segment of RR intervals, and the final rhythm classification is made based on statistical evaluation of the preliminary rhythm classification results obtained from all segments.

Figure 15:
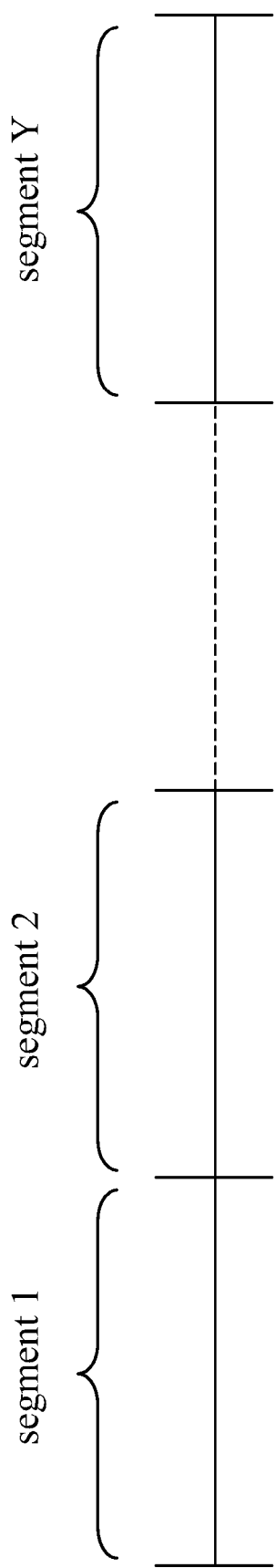
FIG. 15 illustrates multiple segments of RR intervals.

As an example, FIG. 15 illustrates Y segments of RR intervals, where Y is a positive integer (e.g., 4). Each segment contains fixed number (e.g., 16) of RR intervals. As described above, the RdR plot can be constructed from the RR intervals within each segment, then a preliminary AF detection can be made based on the metrics calculated from the corresponding RdR plot. If AF is preliminarily detected in X segments, where X≦Y is a positive integer (e.g., 3) that can be pre-defined or user-programmable, then AF detection is confirmed as the final classification result. Although the segments illustrated in FIG. 15 are non-overlapping, it shall be understood that the same principles also apply to overlapping segments.

Although an exemplary embodiment of the present invention has been shown and described, it should be apparent to those of ordinary skill that a number of changes and modifications to the invention may be made without departing from the spirit and scope of the invention. This invention can readily be adapted to a number of different kinds of medical devices by following the present teachings. All such changes, modifications and alterations should therefore be recognized as falling within the scope of the present invention.

What is claimed is:

1. A heart monitor that processes input signals that represent periodically reoccurring events in a sequence of heart cycles, comprising:
    a signal input;
    an event detector connected to said signal input wherein said event detector is configured to respond to signal features that represent reoccurring cardiac events obtained via said signal input;
    at least one timer connected to said event detector and configured to determine an interval duration or its inverse of a time interval between two successive signal features that represent a cardiac event in respective heart cycles;
    an interval evaluation stage connected to said at least one timer and configured to determine a derivative of said interval duration of two successive time intervals or an inverse thereof;
    a processing stage connected to said interval evaluation stage and said at least one timer and configured to generate graphical data that represents a scatter plot of at least two dimensions, one dimension that represents said interval duration or its inverse and another dimension that represents said derivative of said interval duration or its inverse respectively, wherein the scatter plot comprises data points of which each data point represents the interval duration or its inverse plotted against said derivative of said interval duration with respect to a neighboring interval or the inverse of said derivative of said interval duration respectively;
    an analyzer stage wherein said processing stage is connected to said analyzer stage wherein said analyzer stage is configured to process said graphical data and to detect a cluster of data points in said scatter plot and to generate one or more metric, that depends on a location of one or more clusters of data points in said scatter plot; and,
    said analyzer stage further configured to
        utilize any combination of said generated one or more metric associated with said data points of which each said data point represents the interval duration or its inverse plotted against said derivative of said interval duration with respect to said neighboring interval or the inverse of said derivative of said interval duration respectively, wherein said one or more metric is selected from
        a count of non-zero cells,
        a count of non-zero columns,
        a count of non-zero rows,
        a count of local peaks,
        a total trajectory distance along RR axis,
        a total trajectory distance along dRR axis,
        a distance to global center,
        a distance to positive center,
        a distance to negative center.

2. The heart monitor of claim 1, wherein said signal input is configured to receive any biosignal selected from an electrocardiogram signal, a blood pressure signal, a transthoracic impedance signal, a pulse oximeter signal, a finger plethysmography signal.

3. The heart monitor of claim 2, wherein said signal input is connected or can be connected to at least two sensing electrodes that are configured to pick up myocardial potentials in a heart.

4. The heart monitor of claim 2, wherein the event detector is configured to detect signal features that represent QRS complexes in an electrocardiogram.

5. The heart monitor of claim 2, wherein the event detector is part of an event sensing stage of an implantable medical device.

6. The heart monitor of claim 1, wherein said signal input is configured to receive a marker signal wherein a marker represents the cardiac event.

7. The heart monitor of claim 1, wherein said processing stage is connected to an output configured to display the scatter plot as represented by said graphical data.

8. The heart monitor of claim 1, wherein said analyzer stage is configured to compare the location of one or more clusters of data points in said scatter plot to reference data and to generate the one or more metric, that depends on a similarity of the location of said one or more clusters of data points in said scatter plot to said reference data.

9. The heart monitor of claim 1, wherein said processing stage and said analyzer stage is part of an implantable medical device.

10. The heart monitor of claim 1, wherein said processing stage and said analyzer stage are part of an external device that is configured to be wirelessly connected to an implantable medical device that generates an input signal.

11. The heart monitor of claim 1, wherein said analyzer stage is configured to
extract features associated with said data points in said scatter plot; and,
achieve a rhythm classification based on said features through utilization of a pattern recognition.

12. The heart monitor of claim 11, wherein said pattern recognition comprises a neural network or fuzzy logic.

13. The heart monitor of claim 1, wherein said analyzer stage is configured to process said graphical data through utilization of multiple grids.

14. A method of processing input signals that represent periodically reoccurring events in a sequence of heart cycles, comprising:
obtaining a signal that represents periodically reoccurring events in a sequence of heart cycles;
detecting signal features that represent the periodically reoccurring cardiac events;
determining an interval duration or its inverse of a time interval between two successive signal features that represent a cardiac event in respective heart cycles;
determining a derivative of said interval duration of two successive time intervals or an inverse thereof;
generating graphical data that represents a scatter plot of at least two dimensions, one dimension that represents said interval duration or its inverse and another dimension that represents said derivative of said interval duration or its inverse respectively, wherein the scatter plot comprises data points of which each data point represents the interval duration or its inverse plotted against said derivative of said interval duration with respect to a neighboring interval or the inverse of said derivative of said interval duration respectively;
processing said graphical data and to detect a cluster of data points in said scatter plot and to generate one or more metric, that depends on a location of one or more clusters of data points in said scatter plot;
utilizing any combination of said generated one or more metric associated with said data points of which each said data point represents the interval duration or its inverse plotted against said derivative of said interval duration with respect to said neighboring interval or the inverse of said derivative of said interval duration respectively, wherein said one or more metric is selected from
a count of non-zero cells,
a count of non-zero columns,
a count of non-zero rows,
a count of local peaks,
a total trajectory distance along RR axis,
a total trajectory distance along dRR axis,
a distance to global center,
a distance to positive center,
a distance to negative center; and,
repeating said obtaining the signal, said detecting signal features, said determining the duration, said determining the derivative of said interval duration, generating graphical data, said processing said graphical data and said utilizing said any combination of one or more metric for a plurality of heart cycles.

15. The method of claim 14, wherein said signal that represents periodically reoccurring events in the sequence of heart cycles is an electrocardiogram.

16. The method of claim 14, wherein said signal that represents periodically reoccurring events in the sequence of heart cycles is a marker signal comprising a marker that represents cardiac events.

17. The method of claim 14, further comprising:
comparing said location of one or more clusters of data points in said scatter plot to reference data; and,
generating a rhythm classification output signal that depends on a similarity of the location of one or more clusters of data points in said scatter plot to said reference data.

18. The method of claim 14, further comprising:
extracting features associated with said data points in said scatter plot; and,
achieving a rhythm classification based on said features using pattern recognition.

19. The method of claim 18, wherein said pattern recognition comprises utilizing a neural network or utilizing fuzzy logic.

20. The method of claim 14, further comprising processing said graphical data utilizing multiple grids.

* * * * *